United States Patent
Buschmann et al.

[11] Patent Number: 5,891,025
[45] Date of Patent: Apr. 6, 1999

[54] METHOD OF VALIDATING AND/OR CALIBRATING DEVICES USED FOR CARRYING OUT PHOTOMETRY OF LIVING TISSUES AND A DEVICE FOR IMPLEMENTING SAID METHOD

[76] Inventors: Johannes P. Buschmann, D-81543 Birkenleiten 9; Reinhold Falkowski, D-81669 St.-Cajetan-Str. 32, both of Munich, Germany

[21] Appl. No.: 793,405
[22] PCT Filed: Aug. 22, 1995
[86] PCT No.: PCT/EP95/03337
§ 371 Date: Feb. 24, 1997
§ 102(e) Date: Feb. 24, 1997
[87] PCT Pub. No.: WO96/06343
PCT Pub. Date: Feb. 29, 1996

[30] Foreign Application Priority Data

Aug. 22, 1995 [EP] European Pat. Off. ............... 95/03337

[51] Int. Cl.⁶ ..................................................... A61B 5/00
[52] U.S. Cl. .............................................................. 600/331
[58] Field of Search ..................... 600/310, 322, 600/323, 331; 250/252.1; 356/41, 42, 243

[56] References Cited

U.S. PATENT DOCUMENTS

| 4,834,532 | 5/1989 | Yount . |
| 4,968,137 | 11/1990 | Yount ..................................... 600/323 |
| 5,111,817 | 5/1992 | Clark et al. . |
| 5,278,627 | 1/1994 | Aoyagi et al. . |

FOREIGN PATENT DOCUMENTS 0 314 331  3/1989  European Pat. Off. .
682 627  10/1993  Switzerland .

*Primary Examiner*—Michael Peffley
*Assistant Examiner*—Eric F. Winakur
*Attorney, Agent, or Firm*—Pendorf & Cutliff

[57] ABSTRACT

The invention concerns a process for validation of devices for photometry of living tissue, which encompasses the following steps:

in vitro adjusting of a particular concentration of a substance to be detected in a bodily fluid;

transporting the bodily fluid which has been adjusted to a pre-determined concentration to at least one measuring cell;

transillumination of the bodily fluid; and sensing of the light intensity of at least one spectral window for determination of at least one suitable parameter in the bodily fluid, which is contained in the measuring cell, by means of at least one emitter and at least one receiver;

thereby characterized, that one actively and in a defined manner dynamically changes the effective absorption length through the bodily fluid, without using the bodily fluid for transmission of the forces, wherein the bodily fluid is found in the optical space between the emitter and the receiver; and establishment of at least one relationship between the concentration on the one hand and the suitable parameter on the other hand. This process provides very precise results in the calibration of pulse oximeters. The invention concerns also the device for carrying out the process as well as appropriately calibrated pulse oximeters.

21 Claims, 9 Drawing Sheets

Plethysmography-Simulation Cell

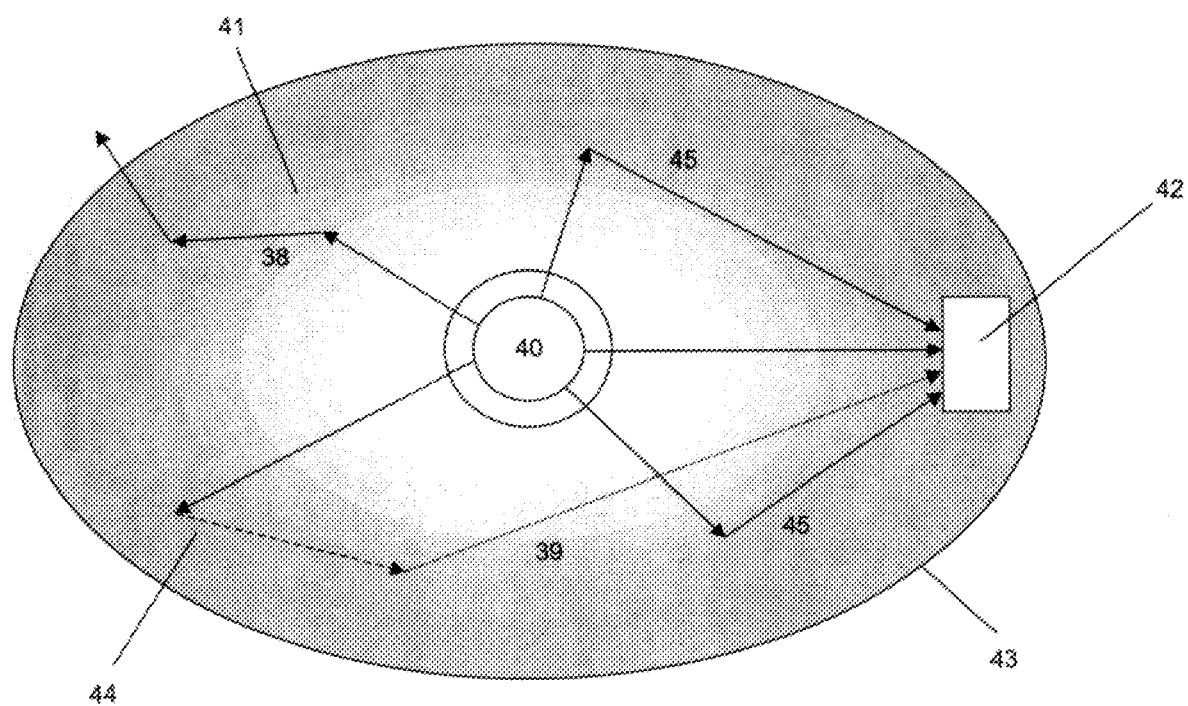
Fig. 1: Scheme of the light path in the calibration chamber

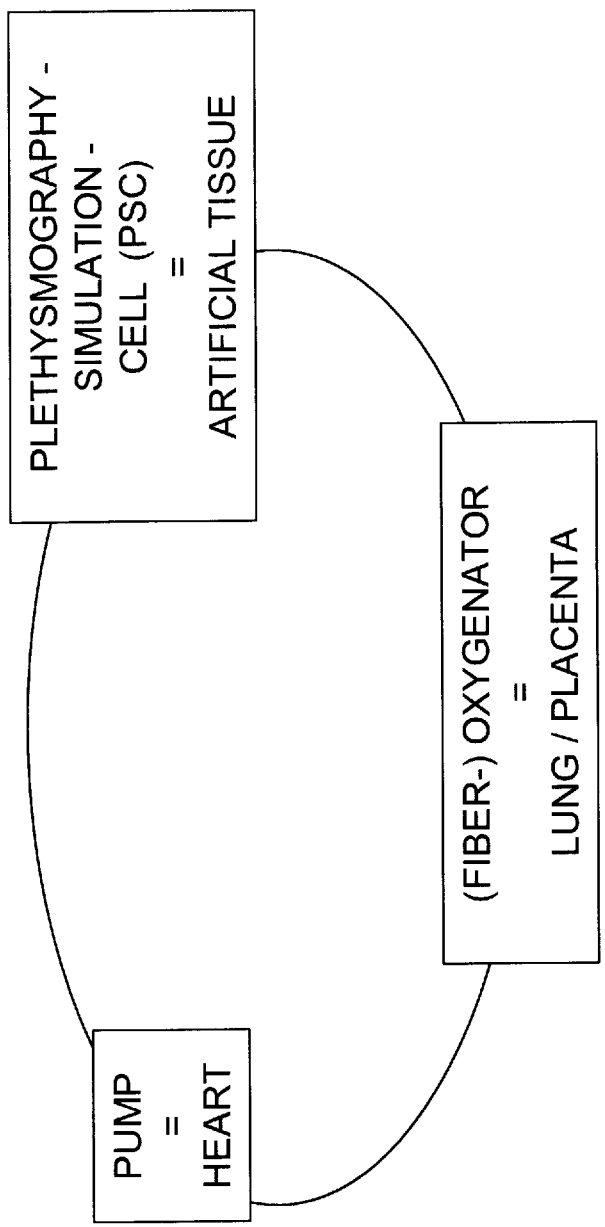
Fig. 2: Schematic calibration system and major components

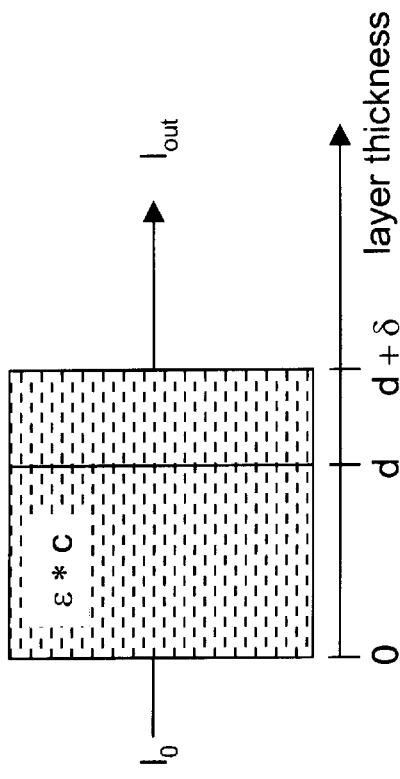
Fig. 3: Principle of light absorption including changes in light path length

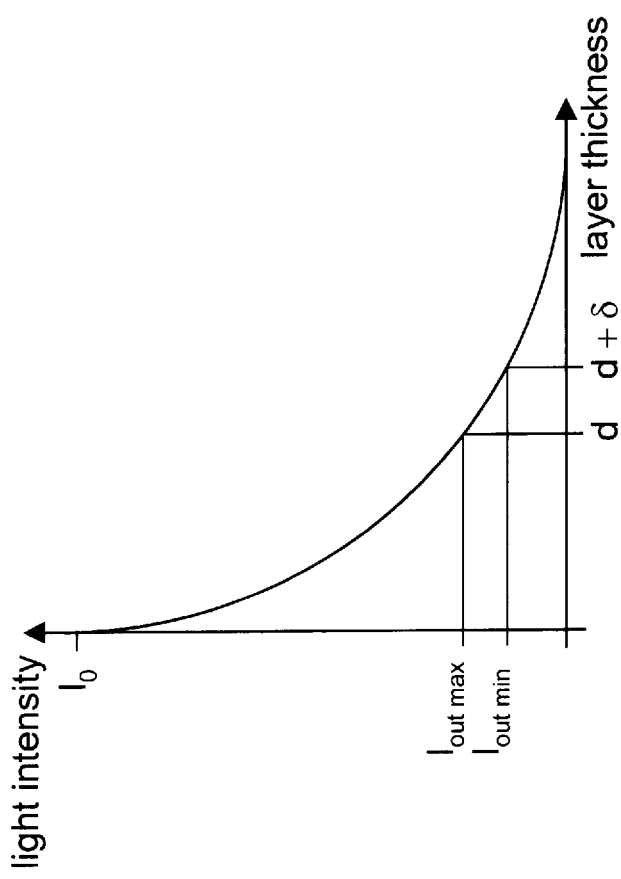
Fig. 4: Idealized process of absorption in dependence upon the layer thickness

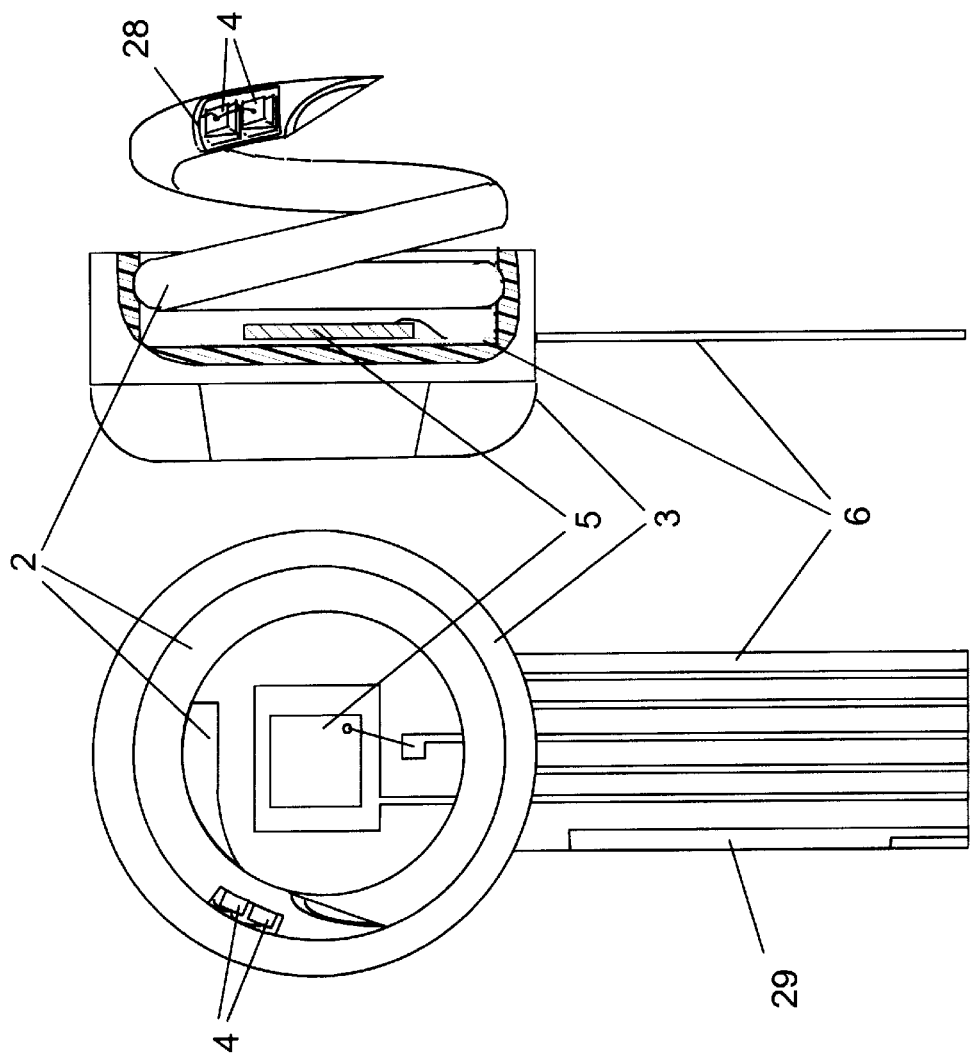
Fig. 5: Example of an embodiment of a transmission sensor for fetal pulse oximetry

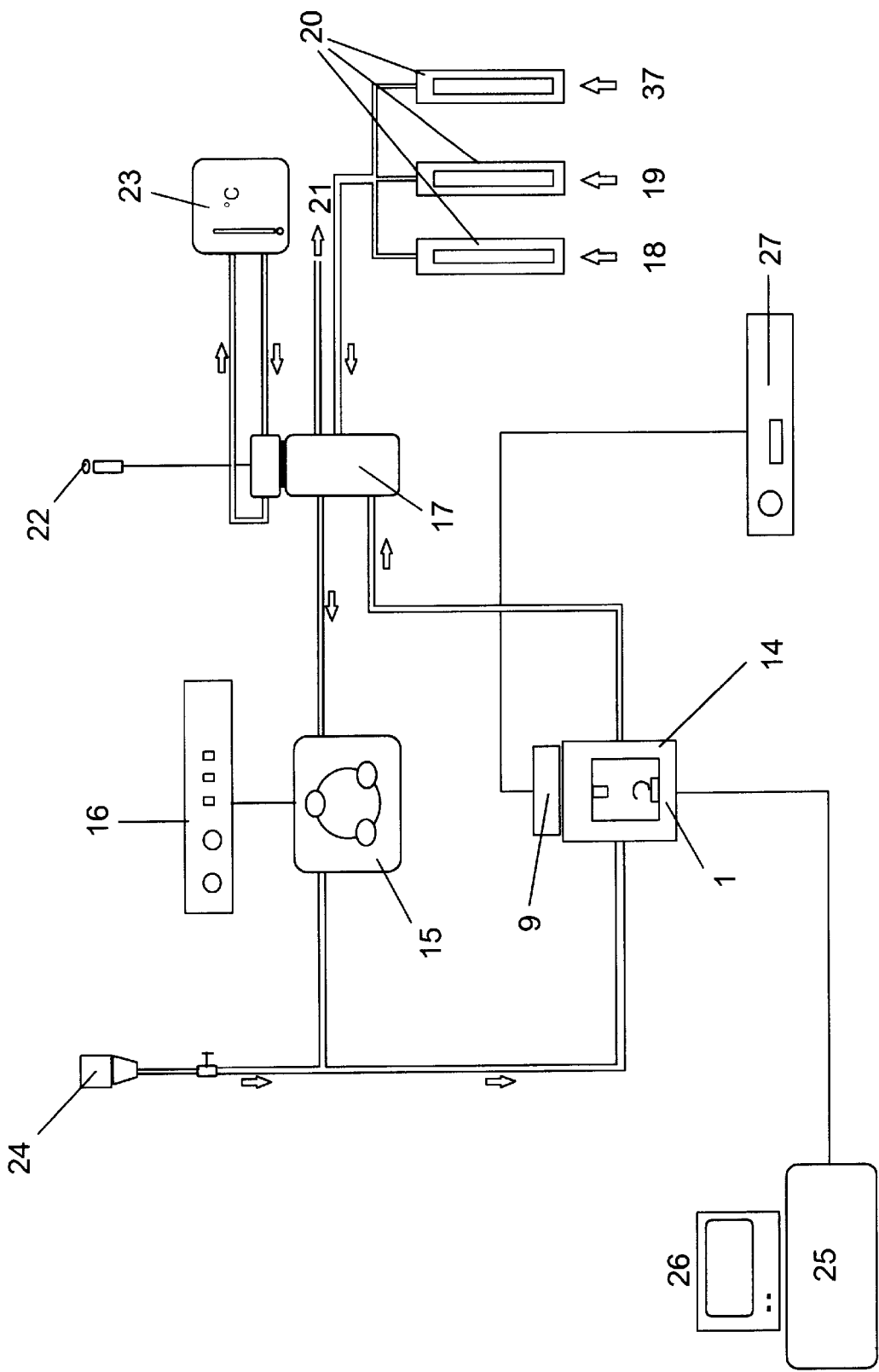
Fig. 6: Calibration system for (fetal) pulse oximetry

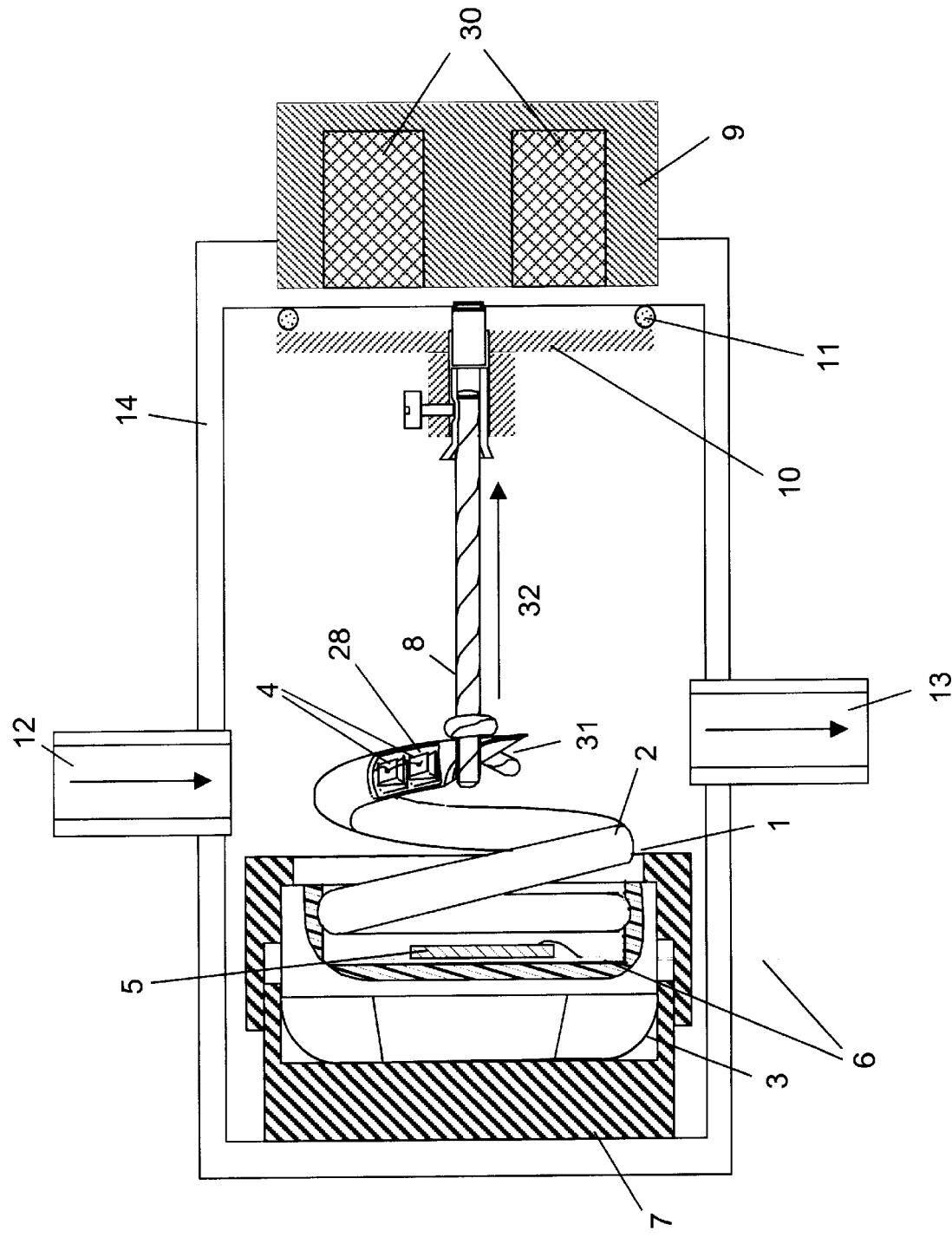
Fig. 7: Plethysmography-Simulation Cell

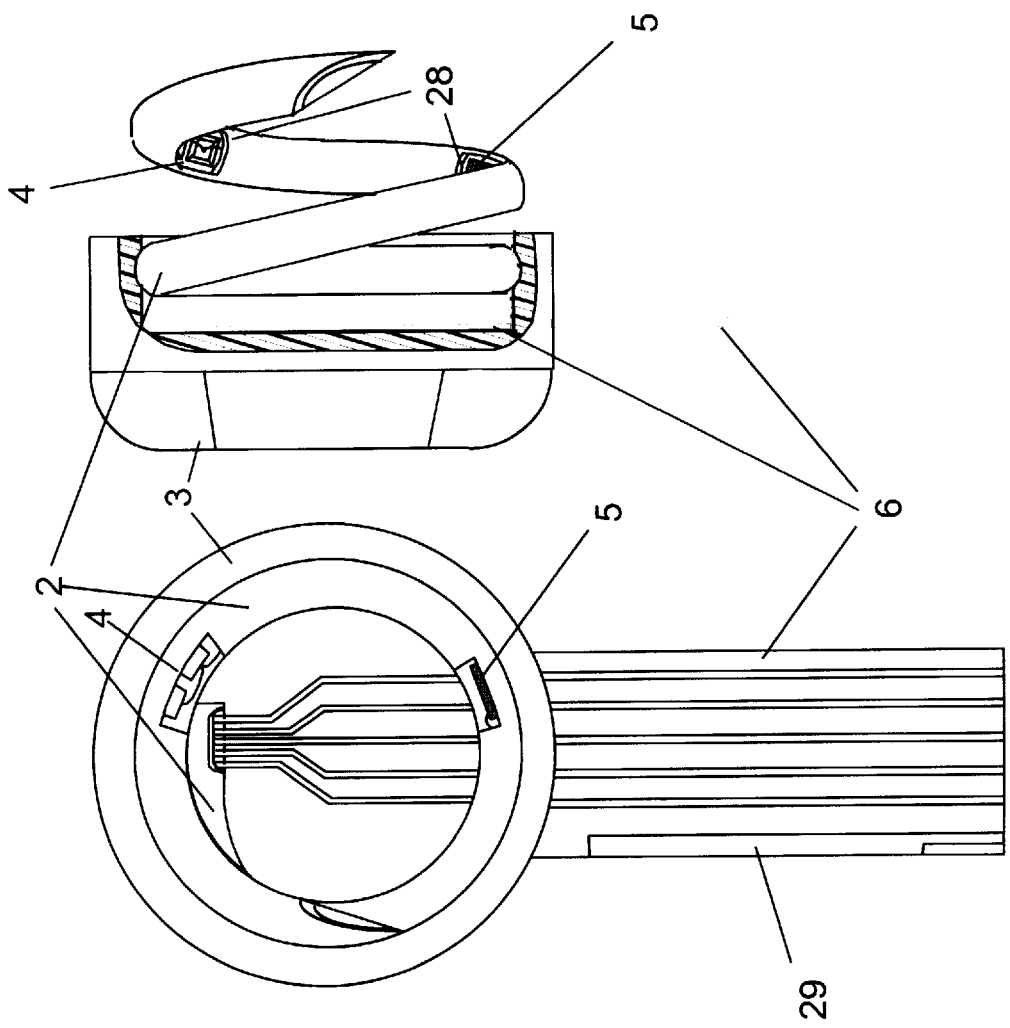
Fig. 8: Example of an embodiment of a transmission sensor for fetal pulse oximetry

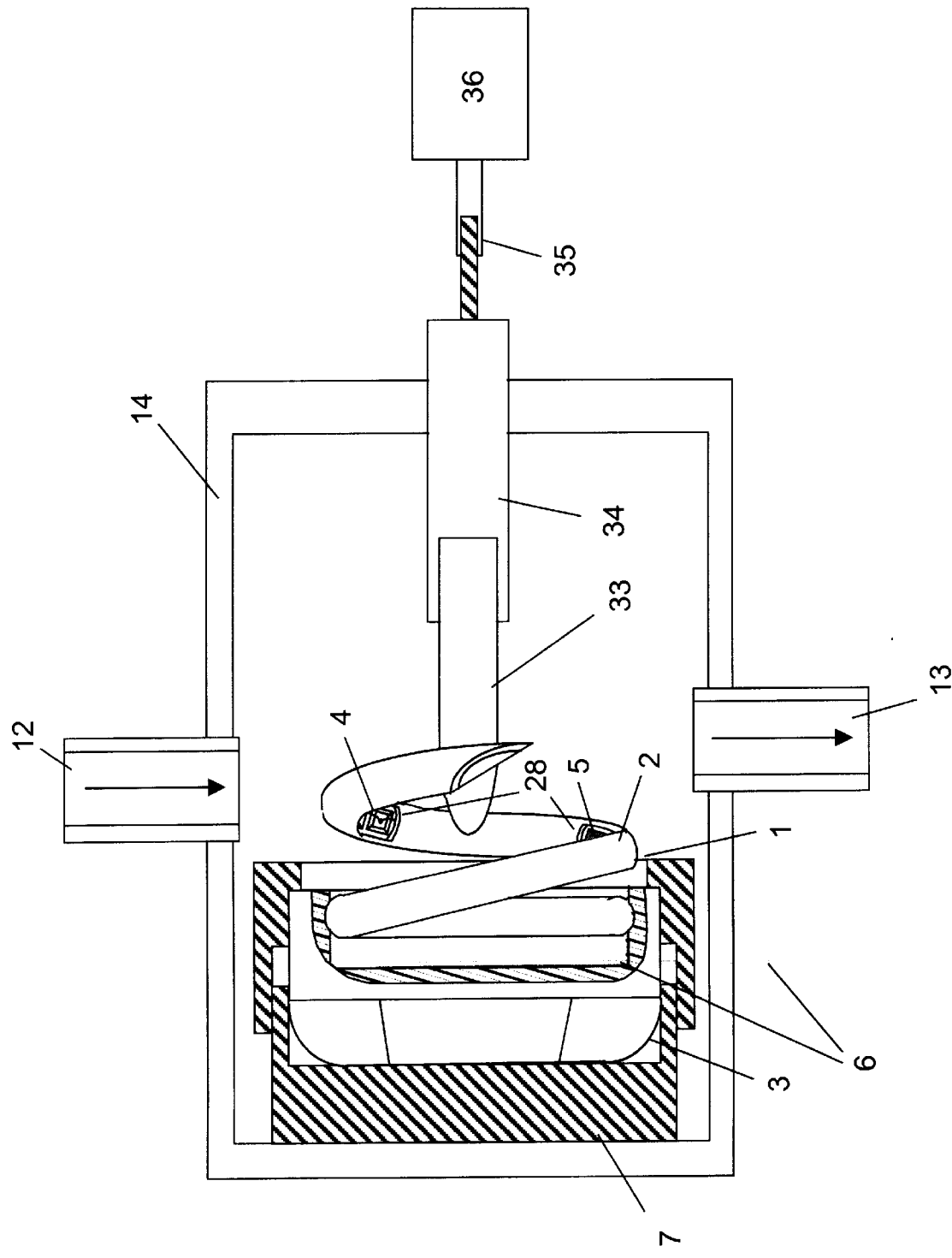

METHOD OF VALIDATING AND/OR CALIBRATING DEVICES USED FOR CARRYING OUT PHOTOMETRY OF LIVING TISSUES AND A DEVICE FOR IMPLEMENTING SAID METHOD

BACKGROUND OF THE INVENTION

Pulse oximetry is a process for measuring arterial oxygen ration. It can be employed in principle in all pulsatile (systolic-diastolic blood pressure) perfused tissues of all species.

Description of the Related Art

Pulse oximetry has been employed clinically with great success for many years. It is no longer possible to imagine operating theaters, intensive care stations, emergency rooms, ambulances, obstetrics wards, etc. without it. Its success rests on its simple operation, the reliable indication and the uncomplicated interpretation of the indicated values.

Pulse oximetry has, until this day, not been available for use as an indicator during delivery. This is remarkable, because oxygen saturation is an essential piece of information for the birth helper, first, in order to make possible the earliest possible diagnosis of problems relating to oxygen condition, and second, in order to evaluate more precisely the classical cesarean section indicators (16% Germany, 20% Europe, 25–33% USA).

It would thus be expected that numerous research groups would be working in order to make this process available for use during delivery. An author of the present patent application has been awarded a pioneer patent for transmission pulse oximetry on unborn fetuses during birth.

During the development of pulse oximetry for assistance in delivery, a particular difficulty has become apparent: calibration. By this, we refer to the achievement of a correlation between the fetal oxygen saturation indicated by the pulse oximeter and the actual arterial oxygen saturation found in the blood of the fetus. Calibration becomes particularly difficult in the fetal area because the fetus already has, or can have, a physiologically very low oxygen saturation. One must thus be able to calibrate, among other things, for very low arterial oxygen saturation levels, which are not reconcilable with those of normal living organisms (be they human or animal), at least not in all situations, in which the brain is included in the low arterial oxygen saturation levels. This does not apply when, for example, a body part, such as an arm, is temporarily isolated for calibration/validation, that is, has a circulation rate differing from the rest of the body which is in correspondence with that of the brain. The fetus is equipped, for this physiological oxygen poor condition, with a special hemoglobin variant, the fetal hemoglobin (HbF). It exhibits a left-biased oxygen binding curve, and thus has a particularly high affinity for oxygen and makes possible therewith even under physiologically non-optimal conditions (prolonged phases of oxygen depletion [e.g., labor pains, expulsion period], difficult diffusion [placenta], mixture of arterial with venous blood [physiological shunt]), bonding with oxygen which makes oxygen ultimately available to the fetal tissue.

Because all pulse oximeters available on the market must be calibrated by the manufacturer, a number of methods have been developed and described in the literature. The calibration over a great oxygen saturation range, as is necessary for the fetal situation, provides, however, a particular requirement or demand on the manufacturer of the respective devices, which cannot be overcome with known methods.

The state of the art describes various calibration methods:

1) Calibration on voluntary subjects:

1. Here young healthy subjects inhale a mixture of oxygen and nitrogen (and carbon dioxide), of which the oxygen partial pressure is stepwise lowered in defined steps from normal values to hypoxic values. After an equilibration is achieved between the oxygen partial pressure in the gas mixture and in the blood, blood samples are taken, from which the oxygen saturation in the arterial blood is determined and at the same time, that is, at the moment the blood is withdrawn, the measured value Omega (see below) is measured with the pulse oximeter to be calibrated. This calibration is thus developed by obtaining as many solid measured values as possible, for which both the oxygen saturation as well as the Omega value is known.

A table or curve is then input into the device, that is, the software of the device, which makes it possible to determine at any measured Omega the corresponding oxygen saturation (Severinghaus/San Francisco: Pulse Oximetry, Springer Verlag, 1986).

2) Another method comprises photometricaly measuring the pulsatile arterial blood in an artificial construct instead of in a living tissue. For example, an artificial finger is made of a red casting resin. A hole is bored into the transplant material into which a shaft is introduced, onto the end of which a slit is sawed. In this slit a red filter disc is wedged. When this test finger is introduced into a pulse oximetry finger sensor and the shaft is rotated, transmission fluctuations are produced as a result of the angular dependent change of the color-dye layer thickness, which can imitate a tissue. As described, depending on the colored dye concentration in the filter disc, oxygen saturation values from 50 to 100% can be imitated. A. J. Munley, A. Shaw, M. J. Sik in *The Lancet*, May 13, 1989. In comparison to an actual finger, no changes occur in the intermediate effective light path between the light transmitter and light receiver, since the finger remains unmoved. This system is very artificial. Often there remains the question of how the test finger itself is to be calibrated.

Because the physiological and/or pathologic oxygen saturation in unborn fetuses can be less than 10%, and such low oxygen-saturation values are not reconcilable with life after birth, there is a requirement for a completely new calibration concept. An essential fundamental principle of this calibration concept must be to find a tissue or, as the case may be, a tissue model, in which the arterial oxygen saturation over the entire range from 100% down to (close to) 0% can be imitated, without any concern that the lack of oxygen saturation affects the validity of the model.

SUMMARY OF THE INVENTION

Beginning with the above-described state of the art it is thus an object of the present invention to provide a process for validation of devices for photometry of living tissues, which makes possible the measurement of the concentration of a substance in a body fluid to be measured over as broad as possible a range of concentrations. The invention solves this problem with the process set forth in claim 1. The dependent claims provide preferred embodiments of the present invention.

Validation means, in the context of the present invention, that the validity (accuracy) of indicated values (measured values) are checked; for example, the validity of the calibration of a pulse oximeter is also included within this concept.

In the calibration method for this invention, the photometry of the bodily fluids relies on very different geometric-optic relationships from those which make up the state of the art. The known techniques employ a hollow body which serves as a cuvette in which it becomes possible to rhythmically modulate the layer thickness, in order to simulate the optical-plethysmorgraphic signal. Thus, devices are known in which absorption fluctuations for imitation of tissue are created by causing pressure modulations in a tube containing blood or another suitable colored fluid, so that this hose undergoes thickness modulations. These thickness modulations resulting from pressure modulations correspond to absorption modulations, which are intended to simulate tissue. In this technique, light emitter, cuvette, and light receiver are arranged as though the photometry is concerned with a non-scattering medium, in which it is fully sufficient that the dye containing solution is somehow provided in a straight light path between light emitter and receiver. However, the blood and, more importantly, the (perfused) tissue is dominated by strongly scattering conditions, the devices according to the state of the art do not accurately represent the conditions in tissue, in particular, the conditions of an invasive fetal pulse oximetry. In order to simulate these conditions as closely as possible, consideration must be given to the following:

1. light leaving the emitter is radiated in all directions,
2. the dye, blood, or blood perfused tissue is present in all spatial directions, and so absorbs as well as scatters,
3. there is not a geometric border such as that produced by a cuvette, but rather the boundaries of the three-dimensionally transilluminated tissue are determined by intensity attenuation, that is, with corresponding light pathlengths, over which the light is attenuated by scattering and absorption, the light intensity is so reduced, that finally it's contribution to the total light signal is irrelevant (one could call this an "intensity limited cuvette" , see FIG. 1).

The simulation of these optical relationships is achieved in accordance with the invention preferably with a device, in which the light emitter and light receiver are provided either on the inside of a more or less completely blood filled hollow body (FIG. 1), or inside respective spectrally neutral scattering bodies, such that the light on the way from the emitter scattering body to the receiver scattering body passes through substantially homogeneous blood, that is, with avoidance of any inhomogeneity of the light conducting path (=optical shunts) and no optical short cuts (shunts) are possible. Through the use of scattering bodies:

1. the scattering level of tissue is achieved, which is significantly higher than that of blood alone, and
2. a substantial independence from the scattering effect of blood is achieved, which can strongly fluctuate with the hemoglobin content, or more precisely, the cell count.

The calibration method according to the invention employs the most consequential simulation of living tissue, in particular, for the simulation of invasive pulse oximeters. In the calibration device according to the invention, for a diffusion scattering medium, such as blood, a measurable, direct light path between light emitter and receiver according to the Labmert-Beer law is more often the exception (very low hemoglobin content, which causes a very low scattering, are here given little consideration) (see FIG. 1). By scattering which is primarily dependent upon tissue and absorption, which is primarily caused by blood, the light intensity from light emitter drops sharply in all directions. Only a part of the blood filled space (=physical cuvette) thus contains (for signal and/or noise) relevant light intensities (intensity limiting cuvette).

Because the light paths are deflected multiple times by scattering, the real relationships are more correctly described by statistical light paths. As a result, the light path between emitter and receiver has a particular distribution and thus a median light path length. Accordingly, there can be determined a median absorption, etc. The direct interfacing of light emitter and receiver becomes irrelevant.

We come now to the dynamic of the light paths, an important element for calibration in pulse oximetry. The suitable device must achieve a change of the light path, in accordance with the invention. We are concerned with the change of the median light path. The effective separation between light emitter and receiver in the above-described light aperture is now rhythmically changed according to the principle of pulse oximetry. This can be achieved in practice, for example, by an actual change in the position of the emitter or receiver, or by the imposition of an optical discontinuity or an optical spacer, for example, a diffuse, color neutral wedge in the blood layer between emitter and receiver, which modifies the "middle effective light path length" or the effective absorption length "through the bodily fluid actively and dynamically in a defined manner, without placing the bodily fluid under conditions of force."

The invention particularly concerns a device for implementing the method of the invention with:

at least one subassembly for adjusting the concentration of a substance to be detected in a bodily fluid;

at least one transport subassembly, with which the bodily fluid adjusted to a specific concentration can be brought to at least one measurement cell;

at least one emitter and at Least one receiver, which are provided in the measurement cell, so that their mean effective light path to each other can be actively and dynamically altered in a defined manner, without requiring the bodily fluid to transmit forces for altering the mean effective light path between light emitter and light receiver; and a device which measures the intensity of light, which has passed through the bodily fluid, detected in at least one spectral window, in a form providing at least one suitable parameter and producing an association between the concentration on the one hand and the parameter on the other hand.

Alternatively the device comprises:

at least one emitter and at least one receiver, which are provided in the measuring cell, wherein in the optical space between emitter and receiver an optical discontinuity of variable thickness is provided.

These devices for validation serve generally for calibration, in particular for in vitro calibration. As to devices, these are as a rule devices for pulse oximetry. The fluid introduced into these devices is preferably blood, in particular, human blood. The concentration of the substance to be determined in the bodily fluid as a general rule is oxygen saturation. In the device according to the invention the emitter emits light of two spectral windows, preferably red and infrared, for the pulse oximetry through the bodily fluid, of which the intensity after traveling through the bodily fluid is detected by means of a photodetector. Particularly preferred for the red range is a wavelength between about 560 and 680 nm and for the infrared range a wavelength of 760–1040 nm. In the device, the median effective light path is varied using magnetic or mechanical forces. The optical discontinuity (with respect to the spectral window) can be in the form of an optically transparent body, such as glass, with repeating varied thickness. This body can be a rotating optically transmissive disk with varying thicknesses or a rhythmically moving wedge. Preferably, for minimization of the non-pulsatile absorption length, the emitter and/or receiver in the bodily fluid, in particular in the blood, is overcoated, wherein the preferred coating is a glass or a plastic, in particular, resin, preferably epoxy resin. The coating can additionally contain particles which are dispersed in the layer coated on the emitter and/or receiver, wherein glass beads, in particular, those of approximately 1 $\mu$m diameter, or titanium dioxide, are preferred.

Preferably, scattering particles are suspended in the bodily fluid, in particular, blood, for a better approximation of tissue characteristics, and, in particular, particles of plastic such as PE (polyethylene), HDPE (high density polyethylene), or the like, which have approximately the same density as the bodily fluid, and which have such a diameter, that they can pass through a fiber oxygenator.

In other words, the invention also concerns a method for optical simulation of human tissue for pulse oximetry, which includes the following steps:

in-vitro setting or adjustment of a particular oxygen saturation value in blood;

transportation of the blood adjusted to a particular oxygen saturation to at least one measuring cell;

measuring a light intensity in at least one spectral window for determination of at least one suitable parameter in the blood, which is contained in the measuring cell, via at least one emitter and at least one receiver, wherein the effective absorption length through the bodily fluid is actively and dynamically altered in a defined way without using the bodily fluid to transmit forces, wherein the bodily fluid occupies the optical space between the emitter and receiver.

Pulse oximeters, which have been calibrated by means of the method according to the invention, have a significant advantage. It may be true that there are pulse oximeters according to the state of the art which externally can not be distinguished from those of the present invention. The accuracy of the indication can however be determined by qualitative comparison of various pulse oximeters. A pulse oximeter which is less accurate as adjusted by state of the art calibration techniques may by chance on one occasion provide a readout which corresponds with reality. For the pulse oximeter according to the invention however this accuracy can be reliably incorporated into the readout, as can not be achieved by the state of the art. It can thus be concluded from the comparison, that the pulse oximeters calibrated in accordance with the inventive method are imparted with a new characteristic.

The subject matter of the invention further includes the measuring cell for use in the validation of a device for pulse oximetry with:

a container with at least one supply and at least one removal opening as well as at least one emitter and at least one receiver for light waves, an effective absorption length through the bodily fluid, which is actively and in a dynamic manner altered in a defined way without using the bodily fluid to transmit forces, wherein the bodily fluid occupies the optical space between the emitter and receiver.

In accordance with the invention, the sensors to be calibrated are introduced into blood that is adjustable to within the known oxygen saturation range (0–10%) (tonometer, [fiber-] oxygenator with mixture of $N_2$, $O_2$, and even $CO_2$) so that the effective lightpath (inclusive of scattering) between the light emitter and the light receiver is completely in blood. Thus, a photometry is produced in which a light path exists between the emitter and receiver that is not defined by the mass of the cuvette, but rather is defined by the fact that the scatter light paths become longer in correspondence to their departure from the direct path between emitter and receiver, until the light intensity finally becomes so small, that it's contribution to the signal becomes irrelevant. One could refer to this as a virtual or a functional cuvette. Thus, there exists a separation of the effective light path with a mean length. If the length of the effective light path in blood is repetitively (for example, periodically) modulated, be this though change of the mean effective light path between emitter and receiver, or through influence of the absorption and/or scattering in the effective light path, so there results a typical signal with a constant and a pulsatile component, so that from a minimum and a maximum of the total signal the interval $\Omega$ (see formula below) can be calculated. One can concretely alter the absorption by, for example, placing an optically transmissive body (for example a wedge shape) dynamically in the light path, which at least in part displaces the absorbing fluid (blood) and therewith changes the effective layer thickness. Alternatively, a static body can be provided, of which the surface optical characteristics, such as reflectivity, change. Also, the mean light path and the effective absorption layer thickness can be dynamically altered. The desired calibration curve is produced by a correlation between the oxygen saturation in the blood and the measured light intensities values for $\Omega$. Using this method, this device is not only suitable for all kinds of pulse oximetry sensors (reflection sensors, transmission sensors), but rather in general for all kinds of applications, in which the concentration of particular substances in fluids and particularly in bodily fluids, such as, for example, photometry of living tissue, are to be determined.

$$\Omega = \frac{\ln\left(\frac{I_{out\,max\,\lambda 1}}{I_{out\,min\,\lambda 1}}\right)}{\ln\left(\frac{I_{out\,max\,\lambda 2}}{I_{out\,min\,\lambda 2}}\right)}$$

The invention was made based upon the following assumptions:

Human experimentation: there are three possibilities for directly employing human tissue for the calibration/validation over a wide range of oxygen saturation ranges while ensuring that the danger of brain damage is avoided:

existing brain damage anencephally decoupling tissue from a healthy brain with it's own circulation system, for example, via a heart-lung machine perfused extremity (armorleg)

[heart-lung-machine→artery→arteriole→capillary→venule→vein→heart-lung-machine]

A completely different application, in which absorption changes are to be generated in perfused tissue with human blood, is the animal experimental model, wherein animal tissue is perfused with human blood. The spectral characteristics of human blood are therewith ideally reconstructed, although the animal tissue differs in many respects, in particular the histological structure, from that of human blood.

A further inventive possibility for calibration, in particular to make invasive fetal pulse oximeter sensors useful for human tissue, is to allow the oxygen saturation of an arterial or venial blocked extremity to slowly fall due to own use and depletion and to practice a type of pulse oximetry, in which one applies artificial mechanical excitation to the sensor, that is, for example, by movement of the sensor itself, which causes changes in layer thickness or as the case may be pressure variations from outside the tissue are conveyed into the tissue (for example, oscillation of a cuff, such as a blood pressure cuff). What is important, is to understand that an essential characteristic of pulse oximetry is being departed from, namely that, the transmission fluctuations are produced by volume fluctuations in the arterioles. In the "capillary bed calibration" the entire tissue is subjected to pressure fluctuations, which causes a displacement of the cumulative vesicles beds: the arteries and arterioles, the capillaries as well as the venules and veins. Accordingly, the indicated oxygen saturation value represents a mixture of the saturations of the various circulatory components in their respective volumetric component parts. Thereby it is particularly advantageous that the capillaries are the only vessels in which a sizeable amount of oxygen exchange with the tissues is possible. The oxygen diffusion in tissue and the use of the oxygen through the tissue leads finally to a continuous decrease in the mixed oxygen saturation. As reference one can consider either a venous or an arterial fiber optic saturation measuring technology placed as far forward distally as possible or mixed blood samples, of preferably constant mix relationships, for example from a finger tip, of the perfusion blocked extremity (of the circulation blocked finger).

However, the state of the art (U.S. Pat. No. 4,883,055) describes a potentially flawed alternative to pulse oximetry with artificial pulses, wherein the described method does not work in this manner as a result of an erroneous understanding of the fundamental pulse oximetry principles.

Animal or human tissue can only be used for an extremely low oxygen saturation when the lack of oxygen cannot lead to brain death. This is either the case, when the brain is dead (brain-dead or anencephaly, wherein however the obtaining of samples is necessarily connected with ethical problems), wherein it is insignificant whether the circulation is natural (heart, lung) or artificial (heart-lung-machine), or when the tissue is not sharing with an endangered brain a common arterial vascular system (decoupled tissue, for example, isolated perfused extremity [artificial circulation: artery→arteriole→capillary→venule→vein→heart-lung-machine]→artery). It is to be noted that hypoxic tissues can behave differently, particularly the arterial vascular tone would not be comparable with tissue under normal conditions. Arterioles are sensitive to oxygen levels and react with a change in vascular tone. With an intact organism, the release of catecholamine is to be expected, which itself also influences the vascular tone. Animal experimental models have, in general, regardless of species, the disadvantageous characteristic that the anatomy of their skin is principally quite different from that of man. There is thus no complete anatomical compatibility. Also, pulse oximetry is based upon chemically specific amounts, the summed spectral absorption co-efficient of both hemoglobin factors, oxyhemoglobin and de(s)oxyhemoglobin. Because these two fractions vary from species to species, it is understandable that their absorption coefficients are also not identical. Even adult and fetal human hemoglobin have different spectra. If one wanted to approach the calibration using animal experiments, one must first measure the corresponding hemoglobin spectrally. As a result, one obtains a calibrated animal pulse oximeter, which provides values that are only valid for that specific species. The human fetal calibration cannot be arrived at from this point.

Although the invention is described using the calibration of a pulse oximeter as an example, it is not limited thereto. The method according to the invention, or as the case may be the device according to the invention can obviously also be used for the measurement of various systems, in which specific light absorbing parameters vary in the bodily fluids to be measured and w hic h can be measured by means of photometry.

The term light as used in this context means not only visible light, but also beyond this the neighboring regions, and in particular infrared.

Natural tissue is not suitable for such extreme low oxygen saturation values because it is difficult to protect the brain that is in the system from the oxygen deprivation, and the unphysiological low oxygen saturation changes the tissue in many respects.

We now describe therefore the discovery of an artificial-tissue model that makes possible each saturation without transitioning between a physiological and a virtual pathologic state. This model satisfies the following characteristics:

It simulates an arterial/arteriole-pulsation in that between light emitter and light receiver a change of distance can be produced, of which the intensity (amplitude) and frequency can be adjusted over a great range.

It simulates the arterial character in that pulsating, arterial blood, that is, blood immediately after the gas exchange in the lung, courses through the tissue model. As a result, each oxygen saturation condition in the blood can be simulated.

It makes possible the application of the fetal transmission-pulse oximetry-sensor (and other reflection sensor and transmission-pulse oximetry-sensors) so that the sensor completely and exclusively evaluates the arterial blood in the tissue model.

It enhances the reproducibility and precision (oxygen saturation, heart frequency, pulse form, pulse harmonics), than is possible with natural tissues. Of particular interest is the sinusoidal-shaped optical plethysmography and the resulting purity of the frequency spectrum.

It makes possible determinations independently of biological characteristics of natural tissue such as edema, hematoma, injuries, and from physiological values, such as blood pressure, heart frequency, blood flow. Each of these values can be adjusted independently and maintained constant.

It avoids the necessity to set the oxygen saturation by means of the lung (brain damaging), that is, a steady state through inhalation of a defined adjusted mixture (nitrogen, oxygen, carbon dioxide).

It makes possible determinations independent of movement artifacts, from outside light sources, temperature variations and restricted perfusion (shock).

It provides the necessary transparency and reproducibility during the tests.

It makes possible the imitation/simulation of any living species in that the species-specific blood (hemoglobin) is being utilized.

Simulation of arterial perfused tissue and/or disruptions for analysis of pulse oximetry devices with electronic, software and sensors In conventional pulse oximetry, two or more light emitting diodes (LEDs) are alternatingly sequentially periodically switched on and therewith the transmission and/or reflection of the radiated light through the arterial perfused tissue is determined. In transmission pulse oximetry, light of at least two wavelengths travels through the arterially perfused tissue and then impinges upon a photo detector. According to the invention, the tissue is replaced by a light non-transmissive palette so that no light from the light emitting diode reaches the photo detector. On this separating palette, in the direction of the LED side of the sensor, is at least two photodiodes and in the direction of the photodiode side of the sensor, is a light emitting diode or a like simulation device for reflection pulse oximetry sensors.
Method of Operation:

When one of the sensor LEDs is activated, a photodiode on the separation palette analyzer receives the unfiltered light and transforms it in a suitable manner to an electrical signal. The second photodiode receives filtered light of the type, that with it's electrical signal the transmitting sensor-LED can be identified (coincidence, exclusion criteria). For example, if an infrared filter is provided before the second photodiode, then it can only see the infrared LED. Red light is so strongly dampened that no sufficient light intensity reaches this photodiode. With this device (unfiltered and filtered light), one can determine how great the light amplitude is and which of the LEDs is irradiating. With multiple optical filters and photodiodes it also becomes possible to distinguish between two LEDs.

The electrical signal of the unfiltered photo diode is, in accordance with the present invention, logically and/or physically separated into two signal parts, which are proportional to the light amplitude of the sensor LEDs.

$$\text{Omega}=(A\text{Cred}/D\text{Cred})/(A\text{Cir}/D\text{Cir})$$

Arterial perfused tissue is completely simulated. The omega-value forms, in most pulse oximeters, the base line or intermediate value for formation of the intidated $SaO_2$ value. The "AC-value", can in a suitable manner, be modified, so that heart beat, perfusion, finger thickness, movement artifacts, smoking and other disturbances can be simulated. With this barrier palette simulator, it is possible to test a pulse oximeter with great accuracy and purposes such as:

final testing for a pulse oximeter manufacturer, monitoring by regulatory authorities, and precise function tests for recurring tests by the end user.

Characteristics of the Present Invention:

separation of the light path, reception of the light amplitude, recognition of which LED is irradiating, multipliers for each individual LED amplitude, multipliers selected so that base absorption, heart beat, perfusion, finger thickness, movement artifacts, smoking, disturbances and other artifacts can be simulated, and generation of a true light signal with one or more LEDs, which is proportional to the initial light and the respective multipliers.

Using known techniques for controlling the sensor, it now becomes possible to control the boundary palette LED so that the sensor photodiode obtains a signal as though a pulsatile perfused tissue were located therein. In addition, the two analyzed sensor LED functions with virtual optical characteristics of an arterial perfused tissue must be multiplied. From the synthesis of the sensor LED control on the side of the pulse oximeter and the modulated tissue characteristics there is produced a signal, which is transmitted from the barrier palette LED to the photodiode of the pulse oximeter, individually the following characteristics can be simulated:

base absorption heart beat perfusion finger thickness motion artifacts smoking disturbances other characteristics The following are the primary elements of the calibration construction according to the invention (see FIG. 2):

1. Pump=Heart:

As an artificial heart, a roller pump was provided. With it, blood was pumped in a circulatory system comprising a pump, oxygenator and artificial tissue corresponding to heart, lung and tissue.

2. Oxygenator=Lung:

As an artificial lung, there can be employed a system that can equilibrate the blood with gases. As a possible example, a fiber-oxygenator was employed (company Terumo, type CAPIOX 308), which equilibrates the blood with an atmospheric or, as the case may be, oxygen/nitrogen-carbon dioxide-gas mixture that can be mixed without restriction. Thousands of thin, porous, plastic tubes surrounded by the gas mixture convey the blood from one end to the other. Through the pores, an easy exchange is possible. The oxygenator further contains a heat exchanger, which is perfused with 37° C. warm water, in order to bring the blood on the venous side to the body temperature so that the oxygen uptake can occur under the physiologically correct conditions. Also, other temperatures can be realized analogously, so that a calibration can be performed for a temperature dependent absorption of the blood.

3. Plethysmographic-Simulation Cell=Artificial Tissue:

The essence of the invention is the artificial tissue. It is comprised, in principle, of a container that is integrated in the circulatory system and through which flows the blood that comes directly out of the oxygenator. A pulse oximetry sensor is securely mounted in the container. A suitable device either causes the mean effective light path between the light emitter and the light receiver or else the absorption layer thickness to vary rhythmically, for instance with the frequency and maybe also with the pulse form of a typical plethysmographic signal. In principle, almost any signal form is possible, and, in particular, a sinusoidal-shaped form is preferred because of it's spectral purity. The pulse oximetry sensor is positioned entirely or at least as much as necessary in the blood in order that the light path between the emitter and the receiver, inclusive of the scatter path, is completely directed through the blood. In this arrangement, each of the pulsatile distance changes or, as the case may be, changes in absorption layer thickness, produces a change in the transmission according to the law of Lambert and Beer, which quite well characterizes these relationships, although many of their preconditions, in particular, the lack of respectively equal scatterings, are not satisfied. As is conventional in pulse oximetry, one measures the transmission variations in both (eventually also in more than two wavelengths some day in order to determine the relative concentrations of even more hemoglobin fractions or of other relevant dyes) hemoglobin fractions. The measured values are then electronically sensed, eventually at some point separated into two channels, converted analog→digital, and specific values are produced, in particular, an intermediate value, which in the literature, is mostly referred to as Omega. The exact mathematical derivation is discussed further on below.

The principle of the tissue model according to the present invention is mechanical, by means of an effective light path change between the light-emitter and light-receiver, in cases under blood, of which the oxygen saturation can be controlled or, be investigated. Pulsations of the mean effective light path from emitter to receiver, for example, are not produced by means of blood pressure amplitude. Instead the sensor is located in the blood and the mean effective light path or, as the case may be, the effective absorption layer thickness is directly mechanically pulsatilely changed. Consequently:

Fully valid values are obtained with no constraint as a result of intolerance of low oxygen saturation condition or, as the case may be, through movement artifacts.

The tissue model is comprised, in one possible embodiment in accordance with the invention, of a chamber (for example, made of metal) with a removable lid. A large pot electromagnet forms one side of the chamber, which, by means of a practically non-extensible thread, causes a change in the mean effective light path and also the transmission changes in the inside of the chamber. In fetal transmission pulse oximetry sensors, the option is available to make use of the restoring force of the spiral spring itself and to simply rhythmically stretch this spring apart. When the magnet is not energized, then the spiral contracts itself and retracts the thread and the displaced magnet anchor (or a pot-core coil) back with it. There are a number of different reasons to keep the blood volume as low as possible: fetal blood is only available in small amounts, particularly when the umbilical chord blood is employed. Besides this, small blood amounts are less sluggish, both in the heat exchanger as well as in the equilibration with gases.

In a further embodiment according to the invention, the variance of the absorption is achieved by introduction of a transparent body, for example a glass wedge or a glass step, which displaces blood. In this manner a blood layer thickness change is produced. A servomotor with an alternating direction of rotation and a coil spool for transformation of the rotation movement into a translational movement moves the optical wedge between light emitter and light receiver. This calibration principle can be used with fetal pulse oximetry sensors in which both light emitter as well as light receiver are placed within the tissue, that is, are introduced via a spiral needle. These so-called inside-inside sensors can be constructed in the following manner: in the part of the spiral, which comes to rest within the tissue in the operational state, two oppositely lying opposing windows are formed in the needle. In one window the two LEDs are provided, and in the other a small photodiode is placed.

The entire system is an artificial circulatory system, that is, the components are positioned analogously to their positions in the circulatory system in the organisms in a circular manner. The blood is thus pumped in a circulatory system.

Theoretical Possibilities of Methods of Calibration:
Comparison of the pulse oximeter indicated oxygen values with a reference.

| TISSUE MODEL | SATURATION RANGE | REMARKS |
|---|---|---|
| Actual tissue with brain (human) | (50) 60–100% | Arterial blood samples, from samples in the steady state, the mixture of $O_2$ and $N_2$ in respiration |
| Actual tissue with brain (animal) | (0) 50–100% | Contingent therefrom that the referenced pulse oximeter indicates correct values (in the steady state) |
| Actual tissue without brain (animal) | (0) 50–100% | In principle good, but limitations of actual tissue (artificial oxygen saturation) |
| Actual tissue without brain (human) for example, anencephaly, brain dead, post-mortal | (0) 50–100% | Ethical problems! Scientifically the best model with actual tissue! Restrictions of actual tissue (artificial oxygen saturation) |
| Plethysmographic simulation with blood (excitation of a pulse oximetry sensor with pulsating, blood-filled tube or hose) | 0–100% | The pulsating blood pressure itself causes the expansion, that is, enlarges the mean effective light path from emitter to sensor. Unavoidable and uncontrollable hose movements result in movement artefacts |
| Non-plethysmographic simulation without blood (other dye stuffs) | Approximately 50–100% (described in the literature) | Only limited values, dye stuff used is not hemoglobin, for each simulated saturation an independent system is necessary, pulse frequency and form are difficult to simulate |
| PLETHYSMOGRAPHI CSIMULATION WITH BLOOD (ANY ORIGIN): PLETHYSMOGRAPHI CSIMULATION CELL = ARTIFICIAL TISSUE = INVENTION | 0–100% full range is usable. For verification of the biological validity of the measured values, comparisons are made with values in the physiological range, which are measured in volunteering subjects. | Pulsations of the effective light path between emitter and receiver are not produced by blood pressure amplitudes, but rather the SENSOR IS IN THE BLOOD and the EFFECTIVE LIGHT PATH IS DIRECTLY MECHANICALLY CHANGED PULSATILY. Consequently: FULLY VALID VALUES and NO LIMITATIONS AS A RESULT OF INTOLERANCE OF LOW OXYGEN SATURATIONS OR, AS THE CASE MAY BE, MOVEMENT ARTEFACTS. |

Pulse oximetry is a continuous photometry of living, arterial, that is, pulsatily blood perfused, tissue typically in two spectral regions. It resides in the fact that hemoglobin is comprised of two fractions, namely as oxygenated hemoglobin and as de-oxygenated hemoglobin.

These two hemoglobin fractions differentiate themselves in their specific spectral absorption, and are thus two different dye stuffs. One is familiar with this from the observation that, for example, veins or hematoma appear to be blue, oxygen poor hemoglobin thus appears to be blue, while in comparison well oxygenated blood, for example, sunburns, inflammations, appear red.

For pulse oximetry, when a tissue is transilluminated, the absolute tissue layer, for example, the thickness of a finger is not known. The obtained oxygen saturation is therefore not determined as an absolute (for example, in grams per liter), but rather is relative: one obtains the percentage of oxygen saturation, that is, the fraction of oxygenated hemoglobin compared to the total hemoglobin.

What is meant by total hemoglobin is, in this sense, the sum total of all measurable hemoglobins, that is, that which is in the two spectral ranges the two factors: oxygenated hemoglobin and de-oxygenated hemoglobin. If there are no other hemoglobins, fractions of significant measurable concentration, then the pulse oximetry measures the reliable values. If, however, for example, the methemoglobin or carboxyhemoglobin exist in high concentrations, then errors imminent in the system result.

Pulse oximetry exists principally in two variants, transmission pulse oximetry and the reflection pulse oximetry, each according to the main path of light. If the light emitter and light receiver are almost completely separated from each other through the tissue, then the tissue is located more or less in the middle between the emitter and receiver. This is referred to as transmission pulse oximetry. A reflection pulse oximetry system has the emitter and receiver essentially on the same side of the tissue outside the skin so that the light emitted from the emitter indirectly reaches the receiver. An essential characteristic of reflection pulse oximetry is also that light reaches the receiver without actually passing directly through the tissue, but rather via an optical shunt (short circuit). As one can deduce from this definition, flowing transmissions are possible when, as a result of special measures, the proportion of shunt-light is made small.

Pulse oximetry measures arterial oxygen saturation. Oxygen saturation is defined as the proportion of oxygen-bonded hemoglobin in the total hemoglobin as follows:

$$\text{oxygen saturation} = \frac{\text{oxygenated hemoglobin}}{\text{total hemoglobin}} = \frac{Hb_{O2}}{Hb_{total}}$$

The concept, "total hemoglobin", can be interpreted as having a double meaning. It depends on whether one understands the summation of oxygenated hemoglobin plus de-oxygenated hemoglobin, and this leads naturally to a different oxygen saturation than when one includes inevitably occurring hemoglobin factors into the sum. In order to better distinguish, two following terms have been created:

fractional oxygen saturation, and functional oxygen saturation.

The most correct definition relates the concentration of oxygenated hemoglobin to the sum of all possible hemoglobin fractions as the total hemoglobin.

$$\text{fractional oxygen saturation} = \frac{\text{oxygenated hemoglobin}}{\text{total hemoglobin}}$$

$$= \frac{Hb_{O2}}{Hb_{red} + Hb_{O2} + Hb_{met} + Hb_{CO} + Hb_S + Hb \ldots}$$

For practical reasons, it is useful to limit the total hemoglobin to two components, the two hemoglobin fractions which are optically measurable with two different wavelengths, oxygenated hemoglobin and de-oxygenated hemoglobin (two wavelength pulse-oximetry):

$$\text{functional oxygen saturation} = \frac{\text{oxygenated hemoglobin}}{\text{oxygenated hemoglobin} + \text{deoxygenated hemogolbin}}$$

$$= \frac{Hb_{O2}}{Hb_{red} + Hb_{O2}}$$

The most useful saturation definition is certainly the fractional oxygen saturation. Nevertheless, the functional oxygen saturation, as determined by pulse oximeters, is clinically very useful (when one does not consider the practically rare and/or low concentration dyshemoglobinemias). For didactic purposes, this problem was trenchantly witty expressed as follows: "pulse oximetry can either measure the real oxygen saturation falsely or the false oxygen saturation correctly". One has decided to measure correctly the false oxygen saturation, because it nevertheless, in most cases, provides clinically relevant results.

Theoretically, it would be possible by means of multiple narrow spectral ranges to measure further hemoglobin fractions (multi-wavelength-pulse oximetry). Pulse oximeters are most frequently not calibrated by the user, but rather are calibrated once by the manufacturer.

By calibration, one understands the production of a correlation between the measured value Omega (mostly used in the literature, for the definition see below) as measured by the pulse oximeter, and the actual oxygen saturation occurring in the tissue. In the latter case, it must be determined by a methodology, which has a known and sufficient measuring precision, that is, substantially exceeding the one of the pulse oximeter to be calibrated. For this, one employs most often the so-called "CO-oximeter" (for example, OSM-3 from Radiometer or ABL-270 from Ciba Geigy Corning) with the help of which one can measure the oxygen saturation of blood samples directly. In principle, there may also be employed blood gas analyzers for determination of the oxygen saturation of blood samples, but they calculate the oxygen saturation from various measured values (partial pressures) making use of several hypotheses. Of course, a higher precision can be expected if a value is measured directly as opposed to a value calculated from indirectly measured ones. In order to calibrate a pulse oximeter with a CO-oximeter, one must have a tissue on which one can employ the pulse oximeter, for example, a finger. Stable oxygen saturations in the arterial blood must be produced by respiration of oxygen-nitrogen mixtures with defined oxygen concentrations within a useful and ethically justifiable realm, so that these oxygen saturations, which are determined from blood samples with a CO-oximeter, can be correlated with the pulse oximeter to be calibrated. Thus, there is a correlation between the known oxygen saturation and the one to be determined. It is the object of these measurements to calibrate the pulse oximeter in such a way that the true situation (with respect to the standard CO-oximeter) is reflected.

The transilluminated tissue can be imagined as consisting of multiple layers, each of which contributes to the total absorption. The following schematic illustrates the most essential layers:

| | |
|---|---|
| pulsating arterial blood → | - systole |
| | - diastole |
| arterial blood | |
| (constant part) | |
| capillary blood | |
| venous blood | |
| bones | |
| tissue (muscle, | |
| connective tissue, | |
| fat) | |
| (incl. pigmented) | |
| skin | |

The Lambert-Beer law describes the absorption of light traveling through an absorptive medium. Although some fundamental pre-conditions for this law are not satisfied (monochromatic light, low concentration, no scattering), the real absorption conditions in pulse oximetry can be described surprisingly well. An increase in the layer thickness of the tissue is responsible for the additional absorption of the tissue during each heartbeat, which can be caused by the supplemental inflowing arterial blood and an expansion of the arterioles. Accordingly, the anatomic responsible structure for the pulse oximetry are the arterioles.

$$I = I_0 * e^{-\epsilon * c * d}$$

where I=intensity of the light after passing through the layer thickness d $I_0$=intensity of the entering light c=concentration of the dye stuff (independent of the wavelength)

d=layer thickness of the absorbing dye stuff (dependent upon wavelength by scattering)

e=specific absorption coefficient (valid for a specific wavelength only)

The pulsatile layer thickness increase can be expressed as follows:

$$I = I_0 * e^{-\epsilon * c(d+\delta)}$$

Result: It is important to understand, that both the constant absorption thickness (d), as well as the pulsatile absorption thickness δ, must contain blood of which the oxygen saturation is to be determined, i.e., the arterial or, as the case may be, the arterialized blood. For this, principally three alternatives come into consideration:

1. Actual human tissue (subjects, patients) of an intact, organism capable of living, normally perfused, that is, by a viable heart,
2. Actual human tissue of an organism not capable of living in the end (brain dead, anencephaly) normally perfused, that is, by means of an intact heart, eventually also artificially perfused (heart-lung machine). Ethics?
3. Animal tissue,
    (a) complete, living animal, naturally perfused, (heart) or as the case may be
    (b) complete, dead, or as the case may be, anesthetized animal, artificially perfused (animal-experimental heart-lung machine)
    (c) body part or organ of an animal of which the vessels are easily accessible, so that it can be artificially perfused (animal experimental heart-lung machine), i.e. be perfused with blood.
4. Artificial tissue, that is, tissue model for pulse oximetry, that at least as a minimal condition possesses the essential characteristics of arterioles, since arterioles are the anatomic structure of tissue pulsatility, and therewith are the cause for the optical plethysmography. The artificial tissue model must also thus at least possess the following characteristics or components:
    (a) hollow chamber,
        which can be perfused with arterialized blood, that is, blood with a defined oxygen saturation
        which at least in one dimension is optically translucent or transparent
        and of which the dimensions, just like expanding arterioles, are pulsatily changeable.

In keeping with these characteristics, there have until now been suggested various artificial tissues. For example, for research of finger sensors, a type of tube was suggested which, filled with blood, is positioned on the inside of a finger sensor. As pressure changes are induced in the tube, there results a change in the tube diameter. This layer thickness change is then registered on the attached pulse oximeter and taken for an optic plethysmographic signal. The oxygen saturation of the changing blood is so determined, which, in the present artificial tissue, is the oxygen saturation of the total transilluminated blood layer. There are further suggestions for producing varying blood layer thicknesses.

Physical Laws and Mathematical Derivations

In the following mathematical section, reference is made to FIGS. 3 and 4. The abbreviations and symbols utilized herein have the following meanings:

$I_0$=incident light intensity $I_{out}$=emerging light intensity c=concentration of the absorbing medium e=extinction co-efficient of the absorbing medium d=layer thickness δ=supplemental layer thickness $$I_{out\ max} = I_o * e^{-\epsilon * c * d}$$

$$I_{out\ min} = I_o * e^{-\epsilon * c * (d+\delta)}$$

Correlating the emerging light intensity ($I_{out}$) with the incident light intensity ($I_o$) provides the relative light as follows:

$$\frac{I_{out\ max}}{I_0} = e^{-\epsilon * c * d}$$

$$\frac{I_{out\ min}}{I_0} = e^{-\epsilon * c * (d+\delta)}$$

If now the ratio of the relative light attenuations is respectively established putting in the thickness d and the d+δ:

$$\frac{\frac{I_{out\ max}}{I_0}}{\frac{I_{out\ min}}{I_0}} = \frac{e^{-\epsilon * c * d}}{e^{-\epsilon * c * (d+\delta)}}$$

$$\frac{I_{out\ max}}{I_{out\ min}} = e^{-\epsilon * c * d + \epsilon * c * (d+\delta)}$$

$$\frac{I_{out\ max}}{I_{out\ min}} = e^{+\epsilon * c * \delta}$$

By logarithmizing of both sides of the equation:

$$\ln\left(\frac{I_{out\,max}}{I_{out\,min}}\right) = = \ln(e^{+\epsilon*c*\delta})$$

$$\ln\left(\frac{I_{out\,max}}{I_{out\,min}}\right) = = \epsilon*c*\delta$$

After this introduction, we consider a system with multiple extinction coefficients and with variable and constant layer thicknesses.

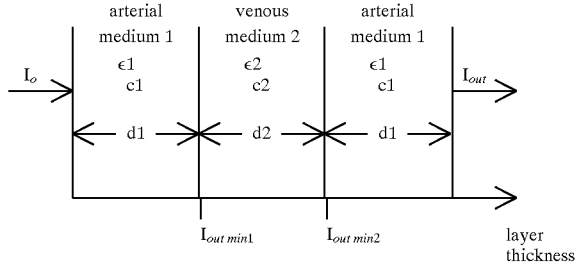

$$I_{out\,min\,1} = I_o * e^{-\epsilon 1*c1*d1}$$

$$I_{out\,min\,2} = I_{out\,min\,1} * e^{-\epsilon 2*c2*d2}$$

$$I_{out\,min} = I_{out\,min\,2} * e^{-\epsilon 1*c1*\delta 1}$$

$$I_{out\,min} = I_o * e^{-\epsilon 1*c1*d1} * e^{-\epsilon 2*c2*d2} * e^{-\epsilon 1*c1*\delta 1}$$

$$I_{out\,min} = I_o * e^{-(\epsilon 1*c1*d1 + \epsilon 2*c2*d2 + \epsilon 1*c1*\delta 1)}$$

$$\frac{I_{out\,min}}{I_0} = e^{-(\epsilon 1*c1*d1 + \epsilon 2*c2*d2 + \epsilon 1*c1*\delta 1)}$$

one obtains the analog $I_{out\,max}$:

$$I_{out\,max} = I_o * e^{-\epsilon 1*c1*d1} * e^{-\epsilon 2*c2*d2}$$

$$I_{out\,max} = I_o * e^{-(\epsilon 1*c1*d1 + \epsilon 2*c2*d2)}$$

$$\frac{I_{out\,max}}{I_0} = e^{-(\epsilon 1*c1*d1 + \epsilon 2*c2*d2)}$$

by developing the ration of $$\frac{I_{out\,max}}{I_{out\,min}}$$

one obtains $$\frac{I_{out\,max}}{I_{out\,min}} = \frac{e^{-(\epsilon 1*c1*d1 + \epsilon 2*c2*d2)}}{e^{-(\epsilon 1*c1*d1 + \epsilon 2*c2*d2 + \epsilon 1*c1*\delta 1)}}$$

$$\frac{I_{out\,max}}{I_{out\,min}} = e^{-(\epsilon 1*c1*d1 + \epsilon 2*c2*d2) + (\epsilon 1*c1*d1 + \epsilon 2*c2*d2 + \epsilon 1*c1*\delta 1)}$$

$$\frac{I_{out\,max}}{I_{out\,min}} = e^{+\epsilon 1*c1*\delta 1}$$

logarithmisation of both sides provides:

$$l_n\left(\frac{I_{out\,max}}{I_{out\,min}}\right) = \ln(e^{+\epsilon 1*c1*\delta 1})$$

$$l_n\left(\frac{I_{out\,max}}{I_{out\,min}}\right) = \epsilon*c1*\delta 1$$

From this derivation it is immediately obvious that all non-changing layer thicknesses and their extinction coefficients, as well as concentrations, were eliminated. It is also seen from the establishment of this ratio 1n $$\left(\frac{I_{out\,max}}{I_{out\,min}}\right)$$

that absolute starting light is elminiated.

If one introduces more absorbing components with various extinction coefficients, then the following is generally true:

$$\ln\left(\frac{I_{out\,max}}{I_{out\,min}}\right) = \sum_n \epsilon_n * c_n * \delta$$

Pulse oximetry is based on this photometric principle. With this type of measurement all constant layers and consequently their extinction coefficients, e.g. of bones, tissue as well as the absolute measuring distance (e.g., finger pad ←→ ear lobe) are eliminated. Only the arterial perfused part is responsible for the pulsating part of the transmission, and, accordingly, the arterial oxygen saturation can be determined.

(Other pulsating components such as venous pulsations or other displacement effects can be ignored.)

Definition of the functional oxygen saturation $SaO_{2\,func}$ $$SaO_{2func} = \frac{Hb_{oxi}}{Hb_{oxi} + Hb_{deoxi}}$$

with Hboxi for the oxygenated and Hbdeoxi for the reduced, deoxygenated hemoglobin or expressed with the corresponding concentrations:

$$SaO_{2func} = \frac{c_{oxi}}{c_{oxi} + c_{deoxi}}$$

Then the functional oxygen saturation $SaO_{2\,func}$ is converted to $C_{deoxi}$ for later use:

$$c_{deoxi} = \frac{c_{oxi}}{Sa_{O2func}} - C_{oxi}$$

$$c_{deoxi} = c_{oxi}\left(\frac{1}{Sa_{O2func}} - 1\right)$$

If one introduces two wavelengths, then one obtains:

$$[\epsilon_{deoxi\lambda 1} * c_{deoxi} + \epsilon_{oxi\lambda 1} * c_{oxi}] * \delta = \ln\left(\frac{I_{outmax\lambda 1}}{I_{outmin\lambda 1}}\right)$$

$$[\epsilon_{deoxi\lambda 2} * c_{deoxi} + \epsilon_{oxi\lambda 2} * c_{oxi}] * \delta = \ln\left(\frac{I_{outmax\lambda 2}}{I_{outmin\lambda 2}}\right)$$

$$\left[\epsilon_{deoxi\lambda 1} * \left(\frac{1}{Sa_{O2func}} - 1\right) + \epsilon_{oxi\lambda 1}\right] * c_{oxi} * \delta = \ln\left(\frac{I_{outmax\lambda 1}}{I_{outmin\lambda 1}}\right)$$

$$\left[\epsilon_{deoxi\lambda 2} * \left(\frac{1}{Sa_{O2func}} - 1\right) + \epsilon_{oxi\lambda 2}\right] * c_{oxi} * \delta = \ln\left(\frac{I_{outmax\lambda 2}}{I_{outmin\lambda 2}}\right)$$

By forming a ratio one obtains:

$$\frac{\left[\epsilon_{deoxi\lambda 1} * \left(\frac{1}{Sa_{O2func}} - 1\right) + \epsilon_{oxi\lambda 1}\right] * c_{oxi} * \delta}{\left[\epsilon_{deoxi\lambda 2} * \left(\frac{1}{Sa_{O2func}} - 1\right) + \epsilon_{oxi\lambda 2}\right] * c_{oxi} * \delta} = \frac{\ln\left(\frac{I_{outmax\lambda 1}}{I_{outmin\lambda 1}}\right)}{\ln\left(\frac{I_{outmax\lambda 2}}{I_{outmin\lambda 2}}\right)}$$

$$\frac{\epsilon_{deoxi\lambda 1} * \left(\frac{1}{Sa_{O2func}} - 1\right) + \epsilon_{oxi\lambda 1}}{\epsilon_{deoxi\lambda 2} * \left(\frac{1}{Sa_{O2func}} - 1\right) + \epsilon_{oxi\lambda 2}} = \frac{\ln\left(\frac{I_{outmax\lambda 1}}{I_{outmin\lambda 1}}\right)}{\ln\left(\frac{I_{outmax\lambda 2}}{I_{outmin\lambda 2}}\right)}$$

Through these ratios, the layer thickness changes are eliminated. Here the measured value $\Omega$ is introduced:

$$\Omega = \frac{\ln\left(\frac{I_{outmax\lambda 1}}{I_{outmin\lambda 1}}\right)}{\ln\left(\frac{I_{outmax\lambda 2}}{I_{outmin\lambda 2}}\right)}$$

as the case may be:

$$\Omega = \frac{\epsilon_{deoxi\lambda 1} * \left(\frac{1}{Sa_{O2func}} - 1\right) + \epsilon_{oxi\lambda 1}}{\epsilon_{deoxi\lambda 2} * \left(\frac{1}{Sa_{O2func}} - 1\right) + \epsilon_{oxi\lambda 2}}$$

this equation is converted to $SaO_2$ in several steps.

$$\epsilon_{deoxi\lambda 1} * \left(\frac{1}{Sa_{O2func}} - 1\right) + \epsilon_{oxi\lambda 1} = \Omega * \epsilon_{deoxi\lambda 2} *$$

$$\left(\frac{1}{Sa_{O2func}} - 1\right) + \epsilon_{oxi\lambda 2}$$

$$\triangledown$$

$$\frac{1}{Sa_{O2func}} [\epsilon_{deoxi\lambda 1} - \epsilon_{deoxi\lambda 2} * \Omega] = \Omega * [-\epsilon_{deoxi\lambda 2} + \epsilon_{oxi\lambda 2}] + \epsilon_{deoxi\lambda 1} - \epsilon_{oxi\lambda 1}$$

$$Sa_{O2func} = \frac{\epsilon_{deoxi\lambda 1} - \epsilon_{deoxi\lambda 2} * \Omega}{\Omega * [\epsilon_{deoxi\lambda 2} - \epsilon_{oxi\lambda 2}] + \epsilon_{deoxi\lambda 1} - \epsilon_{oxi\lambda 1}}$$

Thus, the mathematical relationship of the functional oxygen saturation with the measured value $\Omega$ is illustrated for two different light frequencies. This strict mathematical relationship is valid only for the following preconditions or restrictions:

optically homogeneous medium
no optical scattering
monochromatic light
only the medium to be measured pulsates, or the other pulsating parts can be ignored.

Because of these strict requirements, the functional oxygen saturation can not be calculated in practical conditions. It is determined with the aide of an empirically developed calibration curve.

$$Sa_{O2} = f\left(\frac{\ln\left(\frac{I_{outmax\lambda 1}}{I_{outmin\lambda 1}}\right)}{\ln\left(\frac{I_{outmax\lambda 2}}{I_{outmin\lambda 2}}\right)}\right)$$

This empirical calibration curve takes into consideration all the derivations from the ideal conditions for the validity of the Lambert-Beer law.

In the literature, a simplified equation for the calculation of the measured value $\Omega$ is frequently given. It is derived as follows:

$$\Omega = \frac{\ln\left(\frac{I_{outmax\lambda 1}}{I_{outmin\lambda 1}}\right)}{\ln\left(\frac{I_{outmax\lambda 2}}{I_{outmin\lambda 2}}\right)}$$

$$\Omega = \frac{\ln\left(\frac{I_{outmax\lambda 1}}{I_{outmin\lambda 1}} - 1 + 1\right)}{\ln\left(\frac{I_{outmax\lambda 2}}{I_{outmin\lambda 2}} - 1 + 1\right)}$$

$$\Omega = \frac{\ln\left(\frac{I_{outmax\lambda 1}}{I_{outmin\lambda 1}} - \frac{I_{outmin\lambda 1}}{I_{outmin\lambda 1}} + 1\right)}{\ln\left(\frac{I_{outmax\lambda 2}}{I_{outmin\lambda 2}} - \frac{I_{outmin\lambda 2}}{I_{outmin\lambda 2}} + 1\right)}$$

$$\Omega = \frac{\ln\left(\frac{I_{outmax\lambda 1} - I_{outmin\lambda 1}}{I_{outmin\lambda 1}} + 1\right)}{\ln\left(\frac{I_{outmax\lambda 2} - I_{outmin\lambda 2}}{I_{outmin\lambda 2}} + 1\right)}$$

with the definitions: $DC = I_{outmin}$ and $AC = I_{outmax} - I_{outmin}$ there is:

$$\Omega = \frac{\ln\left(\frac{AC_{\lambda 1}}{DC_{\lambda 1}} + 1\right)}{\ln\left(\frac{AC_{\lambda 2}}{DC_{\lambda 2}} + 1\right)}$$

for $x \ll 1$ there is the solution $\ln(x+1) = x$ $$\Omega = \frac{\frac{AC_{\lambda 1}}{DC_{\lambda 1}}}{\frac{AC_{\lambda 2}}{DC_{\lambda 2}}}$$

For example, with $\lambda 1$=red light and $\lambda 2$=infrared light the following becomes valid:

$$\Omega = \frac{\left(\frac{AC_{red}}{DC_{red}}\right)}{\left(\frac{AC_{infrared}}{DC_{infrared}}\right)}$$

Details of the Tissue Simulation

As shown above, tissues provide optical pathways, which show constant or changing over time absorption, as well as scattering and partially also reflection, dependent on the spectral position and width of the light. Individual components build a total optical pathway.

Blood depleted tissue (for example, after removal of blood by bondaging towards the trunk with an Esmark-S bondage and then "unraveling" and subsequent arterial block or after a rinsing arterio-venous perfusion with an isotonic aqueous solution) appears white and continues to strongly scatter the light. After precipitation (centrifugation) of cellular components, blood is comprised of an almost clear and overwhelmingly colorless aqueous solution. The cellular component strongly scatters the light. Blood (not segregated), as well as tissue, show absorption as well as scatter. Both scattering and absorption, are again dependent on the wavelength. These optical characteristics are true for both transitory optical paths as well as for constant ones. What is important is that the optical characteristics of various relevant anatomic structures can be simulated in detail:

(A) Absorption and scattering and percentage of blood (as part of the bodily fluid) in timewise unchanging tissue can be influenced as follows:

Blood/hemoglobin contributes, depending upon the type and concentration, i.e., concentration distribution of the hemoglobin components [for example, oxygen saturation], largely to absorption and less also to scattering in tissue. One can think of both the scattering as well as the absorption of blood-filled tissue as two distinct, consecutive components, the sequence being irrelevant. If one wants to simulate the component of the (bloodless) tissue, then one can employ a white (color neutral) scattering material, for example, a piece of milk glass. It is ideal, however, to vary the scattering effect independent of the layer thickness. For this, one can employ tiny scatter bodies or centers, for example, small, several micrometer-sized silanized glass beads, approximately the size of erythrocytes dispersed in cast resin. They provide their scattering effect as a result of the disparity in the index of refraction between the two optical media, i.e., scatter centers and surrounding plastic. It is preferable when these scatter centers exclusively scatter, that is, absorb, as little as possible and are thus as transparent as possible. Thus, the light loss is, despite good scattering effect, minimal. If one deliberately wishes to increase the light loss, then one can mix in titanium dioxide in order to cause a stronger scattering combined with a stronger absorption. By balancing the employment of the two scattering components, it becomes possible to construct a scattering/absorption body that one can place in a suitable point along the light path. With this, one can cover a broad range of additional scattering/absorption with which one can make a very flexible simulation of the non-pulsatile total scattering and total absorption of blood-filled tissue.

If one places such a scattering/absorption body in the geometric light path, then it replaces there the bodily fluid (blood) with the following consequences:

The scattering is increased or decreased depending upon whether the scattering effect of the scattering/absorption body is greater or less than the displaced bodily fluid.

The layer thickness of the bodily fluid is decreased. Since, however, preferably the absorption of the scattering/absorption body is selected to lower than the absorption of the bodily fluid, it follows that The bodily fluid-specific absorption falls—the light intensity increases.

With an unchanged pulsatile absorption the modulation depth increases correspondingly.

From the combination of increased light intensity and increased modulation depth, there results an improved signal-to-noise relation.

Therefore, the non-pulsatile absolute absorption, the non-pulsatile scattering and mix, and the modulation depth can be adjusted to a desired and/or tissue optimal simulating value.

Although the position of the scattering/absorption body in the light path is, in principle, irrelevant, there are preferred positions, for example, immediately above the LEDs (light emitter) or above the sensor light receiver. A position in the middle is difficult with respect to the mounting thereof.

(B) Absorption and scatter and percentage of blood (as part of the bodily fluid) in timewise changing, pulsatile tissue can be influenced as follows:

The scattering of blood depends essentially on the proportion of cellular components, that is, on the hematocrit. Accordingly, the simplest influence is changing the hematocrit, which, however, influences both scattering and absorption at the same time. If it becomes necessary to modify scattering and absorption separately, then one can increase scatter and absorption by addition of particles in the sense of suspended particles. They produce tiny scattering centers, for example small, a few mm-large, synthetic spheres, for example having the size of erythrocytes. They attain their scattering influence on the basis of the difference between the index of refraction between the two optical media: scattering center and surrounding blood. The synthetic particles can either scatter or absorb or both. In order to prevent a separation, the specific weight of the particles should be selected to correspond to the bodily fluid. If one is primarily concerned with influencing scattering, then one selects preferably transparent, spherical (bead-shaped) particles of an internal absorption as low as possible. If one desires to change the absorption, one selects particles with an absorption, without color (for example, titanium dioxide) or colored.

These suspended particles shall have a specific weight corresponding most closely to that of blood, so that no decomposition occurs as soon as the blood is not in motion. One should further consider that the addition of scattering particles to blood makes it unusable for CO-oximeter analyses, since the ultrasonic "hemolysis" of these particles can, of course, not be achieved.

The value of the methods of the isolated influencing of scatter and absorption of the bodily fluids lies less in the simulation of the bodily fluids, which by itself is already sufficiently simulated. Moreover, the isolated influencing of a single parameter facilitates the understanding of complex constellations.

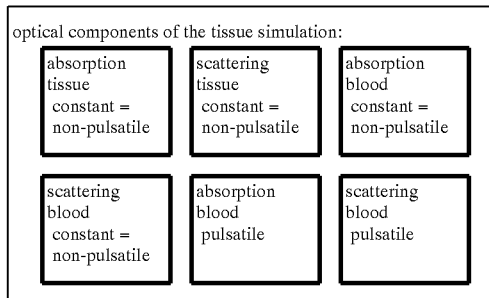

In accordance with the invention the mean effective light path between the emitter and receiver is directly mechanically changed under the condition that the virtual optical cuvette therebetween is filled with the bodily fluid to be analyzed, for example blood, at least to the extent that it is ensured that at least the optical space, in which the changes in mean effective light path take place, is completely filled with the bodily fluid (blood), excepting of course for example an optical displacement body and/or mechanical mounting devices or the like.

It is of further particular significance for the measuring technique that the emitter and receiver need not always be necessarily oriented facing each other, when the bodily fluid has a certain degree of scattering, as is the case in blood. The cells contained in the blood result in a scattering which, dependent from hemoglobin content/hematocrit, permit an indirect light path. Emitter and receiver can even be oriented completely facing away from each other. Above 5 g hemoglobin/dl indirect light paths are possible without any problems. Since the scattering in the natural tissue is measurably greater, it is guaranteed that a sensor construction principle not facing each other does not meet with difficulties.

As a rule, the sensors, and particularly the emitter and receiver, are at least partially surrounded by the bodily fluid. It is however also possible, to orient the emitter as well as receiver parallel above the surface of the bodily fluid, so that practically a reflection measurement is carried out, wherein then the emitter and/or receiver are according to the invention preferably caused to oscillate around their neutral position with a frequency which corresponds to the natural heart rate of the human, so that the natural pulsatile behavior of the tissue, such as a human finger or a human earlobe, is imitated as far as the measurements are concerned.

| Optical characteristics to be simulated | Decreasing of the optical properties | increasing of the optical properties |
|---|---|---|
| Pulsatile absorption | Reducing of the Hb/Hk | increasing of the Hb/Hk |
| Pulsatile scattering | not possible (except for through the reduction of the Hb/Hk) | besides an increase of the Hb/Hk: the addition of scatterirng suspended particles to the blood (suspended particles should have a specific weight which is as close as possible to that of blood) |
| nicht-pulsatile Absorption | Introduction of optical media into the light path with as low as possible absorption, for example, glass or epoxy resin body | not practicable in principle: introduction of optical media in the light path with high absorption, for example, colored glass |
| non-pulsating scattering | Introduction of optical media into the light path having low scattering with relation to tissue, for example, milk glass or glass beads embedded in epoxy resin bodies (different indices of refraction is a pre-condition) | media in the light path with high scattering in comparison to tissue, for example, milk glass or glass beads embedded in epoxy resin (different indices of refraction is a pre-condition) |

BRIEF DESCRIPTION OF THE DRAWINGS:

The present invention will now be described in detail by reference to the figures.

FIG. 1 schematically shows the light path in the calibration device according to the invention.

FIG. 2 schematically shows the inventive calibration structure.

FIG. 3 shows the principle construction of an absorption cell in particular for pulse oximetry (theoretical).

FIG. 4 again shows a typical idealized process of the absorption in such a cell in dependence upon the layer thickness.

FIG. 5 (not true to scale) shows an illustrative embodiment of a transmission-sensor for fetal pulse oximetry.

FIG. 6 (not according to scale) shows a calibration system for the (fetal) pulse oximetry.

FIG. 7 (not according to scale) shows the plethysmography simulation cell wherein the sensor mount securely and immovably fixes the sensor.

FIG. 8 shows an alternate embodiment of a transmission sensor for fetal pulse oximetry.

FIG. 9 shows an alternate embodiment of a plethysmography-simulation cell.

DETAILED DESCRIPTION OF THE INVENTION

FIG. 1 schematically shows the light path in the calibration device according to the invention. Blood represents blood or a blood substitute (generally an aqueous dye solution). Surrounding a light source (40) there is a light scattering diffusing dye material. The arrows show the path of travel (scattered and non-scattered components) within the measuring device. The rays impinging upon the photodiode (FD) are shown and evaluated. There is produced in the inventive device a virtual cuvette (VK; distance from the light source at which the returning components of the light are too weak). The diffuse scattering dye material layer is entirely comprised of the relevant space filled by the optically relevant scattering.

FIG. 2 schematically shows the inventive calibration structure.

FIG. 3 shows the principle construction of an absorption cell, in particular, for pulse oximetry (theoretical). FIG. 4 again shows a typical idealized process of the absorption in such a cell in dependence upon the layer thickness. FIG. 5 (not true to scale) shows an illustrative embodiment of a transmission-sensor (1) for fetal pulse oximetry, as described in patent document DE 3810008 C1. It is comprised of a spiral shaped canula (2) which is embedded in, or as the case may be, glued in, a sensor body (3). In the steel spiral (2), a window is provided, in which LEDs (4) serving as a light source are glued in with a transparent adhesive or bonding agent. On the floor of the sensor body (3), a photodiode (5) is mounted, which is separated only by a thin, optical transparent layer, from the skin surface and lies thereon, when the spiral shaped canula is screwed into the child's scalp. In this way, a piece of living tissue is disposed between the LEDs (4), which are positioned inside the tissue, and the photodiode (5), which rests upon the scalp. Both the LEDs (4), as well as the photodiode (5), are connected to a sensor cable (6), which, for example, is comprised of a cable or, as shown here, a flexible connection. The sensor cable (6) can, in addition, serve as a EKG-pole. The further reference numbers have the following meaning:

28=window

29=contact surface

FIG. 6 (not according to scale) shows a calibration system for (fetal) pulse oximetry. The main components of this system are the roller pump (15), which is employed as an artificial heart, the fiber oxygenator (17), which equilibrate blood with a gas mixture from a precision stream regulator (20) and the plethysmography-cell (14) which contains the sensor (1) to be calibrated. The precision regulator (20) produces, by means of a flow-regulator for oxygen (18) and a flow-regulator for nitrogen (19), a nitrogen-oxygen-carbon dioxide-gas mixture, which has an oxygen concentration of approximately ½–5%. This gas mixture flows through a fiber oxygenator (17) and flows freely away as vent gas (21). By means of oxygenator (17) and as a result of the plethysmography-cell (14), blood is pumped in a circulatory system by means of roller pump (15) with a drive unit (16)(stepmotor). In addition, it must be ensured that the blood for the equilibrating in the fiber oxygenator (17) has a defined temperature. This is accomplished by means of a temperature stabilizing water bath (23), which pumps water of a constant temperature through the heat exchanger of the fiber oxygenator (17). The roller pump (15) is controlled by means of drive unit (16), so that the correct blood flow in the circulation is accomplished by the roller pump (15), plethysmographic simulation cell (14), and fiber oxygenator (17). Because blood has a tendency to foam, it may require a vent (22), which may be opened for short periods as necessary.

The further reference numerals have the following meaning:

24=blood reservoir

25=pulse oximeter

26=indicator or display

27=power supply for powering magnet

FIG. 7 (not according to scale) shows the plethysmography simulation cell (14). A sensor mount (7) fixes the sensor (1) securely and immovably. Because the spiral shaped cannula (2) has the mechanical properties of a spring, the mean effective light path of the LEDs (4) from the photodiode (5) can be varied by pulling on the tip of the needle. This pulling is effected by an electromagnet (9) having a magnet yoke (10) and is elastically dampened by means of an elastic O-ring (11). A nonelastic pull thread (8) conveys the movement of the magnet yoke (10) onto the needle tip. If one sends repetitive current to the electromagnet (9), so then the tip of the spiral shaped cannula (2) is rhythmically moved. Because the entire plethysmographic simulation cell (14) is irrigated by means of the blood inlet (12) and the blood outlet (13), blood is provided between the light source (4) and the light receiver (5). There results a repetitive, for example, periodically changing thickness of the layer of blood, which is the bodily fluid to be photometrically measured between the LEDs (4) and the photodiode (5). Because the pulling with the nonelastic pull thread (8) accomplishes a movement in only one direction, that is, no pushing movement, it is thus preferred to pretension the spiral shaped cannula, for example, in the case that one has a constant pull on the magnet yoke (10) by means of an equal tension (offset) via an electromagnet (9). The pretensioned path stretch should be greater than the half amplitude of the repetitive travel.

FIG. 9 shows an alternate embodiment of a plethysmography-simulation cell.

The further reference numerals have the following meaning:

3=sensor body

6=sensor cable

28=window

30=magnet coil

31=needle with pull thread adhered thereto

32=direction of pull

In the practical application of the invention, it has become increasingly apparent, that for the perfect tissue simulation in the calibration cell, a large measure the opacity must also be taken into consideration. The diffusion effect of blood is astonishingly small—apparently in blood the light path maintains intact for long distances. The greatest contributor to the diffusion effect over distances in the tissue is not blood, but rather the tissue itself. If one translates this to the relationships or conditions in the calibration chamber, the diffusion must either be replicated before the LED window, or before the photodiode window, or by the modulator (wedge).

There are principally two possibilities for the production of optical diffusion:

a) In one embodiment, an abrasion creates a high outer surface discontinuity and diffuses the light on the various fascets of this uneven surface. Thereby, only a single scattering index is considered, if one does not take the index of refraction of the glass, for example, from air or from blood/water, into consideration.

b) In a second embodiment, diffusion is accomplished by multiple transitions between varying indices of refraction. For example, glass pearls, which are coated with a synthetic resin can be provided that function as a light distracting structure, wherein the number of these distraction centers in comparison to abrasion, as discussed above under subparagraph a), is comparatively small. In agreement with the small number of distraction centers, the light loss from such an arrangement is surprisingly small.

In an experiment with UV-hardened synthetic epoxy resin, in which glass spheres were enclosed, it was determined, that silanized glass spheres are not as economical as 3M-Glassbeads, which are hollow, that is, air filled, glass spheres (like transparent subminiature Christmas tree decorating balls). An extremely high diffusion effect is achieved so that during the transition of a light beam through the hollow glass ball multiple changes in index of refraction occur. Light must first go from the plastic to the glass, from glass to the air, and from air back into glass, and from glass back to plastic. Thus, three indices of refraction come into play (as can be seen from the plasma: that of the plastic resin, that of the glass wall, and finally that of the enclosed air).

Diffuse glass wedges were produced as follows:

Duron full glass rods with 3 mm diameter were ground at one rod end, wherein one tensioned the glass rod into a hand drill and pressed against the tip with wet 40 $\mu$m sand paper using the index finger tip and thumb. The roughened glass rod tip (better adhesiveness to epoxy resin being the intended result of roughening) was now coated with glass sphere containing epoxy resin (⅓ glass beads, ⅔ epoxy resin [percent given in volume percent]) layer by layer, whereupon, attention was given to ensure that the glass bead-epoxy resin mixture lengthened the tip of the glass rod by about 5 mm. At the same time, care was given to ensure that the epoxy resin only extended inconsequentially beyond the thickness of the glass rod. After the respective applications of the glass bead-epoxy resin mixture, there is a generous application and somewhat more of UV-light for hardening. At the conclusion, the glass end is ground with a diamond tip until it is somewhat wedge shaped with a planar end surface in which the sensor spiral can project into. From the grinding, the now planar tip of the wedge exhibits the full diffusion effect, that is, even at the front tip of the wedge, no light occurs in the forwards direction.

The glass wedge looks like a glass match with a white head. with a tight, only minimally divergent helium-neon-laser it is tested, whether upon irradiation upon the head of the wedge any light can be detected traveling in the forwards direction (for example, on a 1 meter distanced wall). If the beam is completely broken, that is, the match glows substantially red, the light beam on the wall has completely vanishes and not the smallest traces remain to be seen, then the wedge is judged to be a "success". With such a wedge, we carried out a calibration chamber experiment and determined a calibration curve for a 660/940 nm Inside-Inside sensor and determined an omega value of from 0.3–3.95 for saturations between 100 and 0%, which quite obviously lie on an only slightly skewed curve (hyperbolic or parabolic) and which provided an extremely minimal departure from standard.

| Legend: | |
|---|---|
| 1 = | sensor |
| 2 = | spiral shaped canule |
| 3 = | sensor body |
| 4 = | LEDs |
| 5 = | photodiode |
| 6 = | sensor cable |
| 7 = | sensor mount |
| 8 = | inelastic thread |
| 9 = | electromagnet |
| 10 = | magnet yoke |
| 11 = | elastic o-ring |
| 12 = | blood inflow |
| 13 = | blood outflow |
| 14 = | calibration cell (artificial tissue) |
| 15 = | roller pump (artificial heart) |
| 16 = | drive for roller pump (step motor) |
| 17 = | fiber oxygenator (artificial lung) |
| 18 = | nitrogen supply |
| 19 = | oxygen supply |
| 20 = | precision flow regulator |
| 21 = | off gas |
| 22 = | ventilation |
| 23 = | thermally stable water bath |
| 24 = | blood supply |
| 25 = | BLM-pulse oximeter |
| 26 = | indicator or display |
| 27 = | power supply for magnet activation |
| 28 = | window |
| 29 = | contact surface |
| 30 = | magnet winding |
| 31 = | needle with pull thread adhered thereto |
| 32 = | direction of pull |
| 33 = | diffusing glass wedge |
| 34 = | wedge mount |
| 35 = | coupling |
| 36 = | motor |
| 37 = | $CO_2$ supply |
| 38 = | emitted beam |
| 39 = | light, too weak with respect to the total measured signal |
| 40 = | light source |
| 41 = | blood or fluid with dyestuff dissolved therein with the concentration "c", scattering medium precondition |
| 42 = | photodiode |
| 43 = | physical cuvette wall |
| 44 = | virtual cuvette wall |
| 45 = | scattered beams |

We claim:

1. A process for in vitro validation of a photometric device, said method comprising:
   (a) specifying a substance of a body fluid to be measured;
   (b) adjusting a parameter of said substance of a body fluid in body fluid in vitro;
   (c) providing adjusted body fluid from step (b) to a measuring area within a measuring cell such that at least some of said adjusted body fluid is between a radiation emitter and a radiation receiver, wherein at least one of said radiation emitter and radiation receiver is immersed within said body fluid, and wherein the mean light path between the radiation emitter and radiation receiver corresponds to the effective absorption length;
   (d) transilluminating the body fluid in the measuring area;
   (e) actively and in a defined manner periodically changing the effective absorption length through the body fluid between the radiation emitter and receiver, without using the body fluid as a medium for transmission of forces;
   (f) detecting changes in light intensity of at least two spectral frequencies which are characteristic absorption frequencies for said substance of a body fluid to be detected, said changes constituting a ratio "$\Omega$" of said substance of a body fluid to be detected, wherein $\Omega$ is defined with the following equation:

$$\Omega = \frac{\ln\left(\frac{I_{out\,max\,\lambda 1}}{I_{out\,min\,\lambda 1}}\right)}{\ln\left(\frac{I_{out\,max\,\lambda 2}}{I_{out\,min\,\lambda 2}}\right)} ; \text{ and}$$

(g) determining a correlation between (i) said ratio $\Omega$ and (ii) a parameter of said substance of a body fluid.

2. A process as in claim 1, wherein said parameter is concentration.

3. A process as in claim 1, wherein said parameter is saturation.

4. A process according to claim 1, wherein said photometric device is a pulse oximeter.

5. A process according to claim 1, wherein said validation is in vitro calibration of a pulse oximeter.

6. A process according to claim 1, wherein said body fluid is human blood and wherein said substance of a body fluid to be determined is oxygen.

7. A process according to claim 1, wherein said radiation emitter emits light in at least one red spectral region and at least one infrared spectral region.

8. A process according to claim 1, wherein the change in the effective absorption length is caused by changing the mean effective light path between emitter and receiver, with said emitter and receiver remaining stationary.

9. A process according claim 1, wherein said correlation is an evaluation of the relationship between (i) $\Omega$ and (ii) oxygen saturation.

10. A process as in claim 9, wherein said oxygen saturation is the functional oxygen saturation ($SaO_{2func}$) according to the following equation:

$$SaO_{2(func)} = \frac{cHB_{oxi}}{cHb_{oxi} + cHb}$$

and wherein the following equation is employed for calibration or after producing a calibration curve:

$$SaO_{2(func)} = f(\Omega).$$

11. A process for in vitro validation of a photometric device, said method comprising:
   (a) specifying a substance of a body fluid to be measured;
   (b) adjusting a parameter of said substance of a body fluid in body fluid in vitro;
   (c) providing adjusted body fluid from step (b) to a measuring area such that at least some of said adjusted body fluid is between a radiation emitter and a radiation receiver, wherein the mean light path between the radiation emitter and radiation receiver corresponds to the effective absorption length;
   (d) transilluminating the body fluid in the measuring area;
   (e) actively and in a defined manner periodically chancing the effective absorption length through the body fluid between the radiation emitter and receiver, without using the body fluid as a medium for transmission of forces;

(f) detecting changes in light intensity of at least two spectral frequencies which are characteristic absorption frequencies for said substance of a body fluid to be detected, said chances constituting a ratio "Ω" of said substance of a body fluid to be detected, wherein Ω is defined with the following equation:

$$\Omega = \frac{\ln\left(\frac{I_{out\,max\,\lambda 1}}{I_{out\,min\,\lambda 1}}\right)}{\ln\left(\frac{I_{out\,max\,\lambda 2}}{I_{out\,min\,\lambda 2}}\right)} ; \text{ and}$$

(g) determining a correlation between (i) said ratio Ω and (ii) a parameter of said substance of a body fluid, wherein the change in the effective absorption length is caused by changing the physical distance between said emitter and receiver.

12. A process for in vitro validation of a photometric device, said method comprising:
(a) specifying a substance of a body fluid to be measured;
(b) adjusting a parameter of said substance of a body fluid in body fluid in vitro;
(c) providing adjusted body fluid from step (b) to a measuring area such that at least some of said adjusted body fluid is between a radiation emitter and a radiation receiver, wherein the mean light path between the radiation emitter and radiation receiver corresponds to the effective absorption length;
(d) transilluminating the body fluid in the measuring area;
(e) actively and in a defined manner periodically changing the effective absorption length through the body fluid between the radiation emitter and receiver, without using the body fluid as a medium for transmission of forces;
(f) detecting chances in light intensity of at least two spectral frequencies which are characteristic absorption frequencies for said substance of a body fluid to be detected, said changes constituting a ratio "Ω" of said substance of a body fluid to be detected, wherein Ω is defined with the following equation:

$$\Omega = \frac{\ln\left(\frac{I_{out\,max\,\lambda 1}}{I_{out\,min\,\lambda 1}}\right)}{\ln\left(\frac{I_{out\,max\,\lambda 2}}{I_{out\,min\,\lambda 2}}\right)} ; \text{ and}$$

(g) determining a correlation between (i) said ratio Ω and (ii) a parameter of said substance of a body fluid, wherein the change in the effective absorption length is caused by displacement of at least part of said body fluid in the mean effective light path between said radiation emitter and radiation receiver by an optically neutral displacement body which is more transparent at the spectral frequency at which changes in light intensity are being measured than said body fluid containing said substance to be detected and wherein said displacement body is moved between at least a first position and a second position.

13. A process according to claim 12, wherein said displacement body is a diffuse glass wedge.

14. A process according to claim 12, wherein said displacement body is a rotating optical transparent disc with varying thickness.

15. A process according to claim 12, wherein light scattering particles are dispersed in a coating layer associated with said emitter and/or receiver, and wherein said particles are selected from the group consisting of glass beads and titanium oxide.

16. A process according to claim 15, wherein said displacement body is periodically moved, generating a pulsatile variation in effective absorption length through said body fluid containing said substance to be measured.

17. A process for in vitro validation of a photometric device, said method comprising:
(a) specifying a substance of a body fluid to be measured;
(b) adjusting a parameter of said substance of a body fluid in body fluid in vitro;
(c) providing adjusted body fluid from step (b) to a measuring area such that at least some of said adjusted body fluid is between a radiation emitter and a radiation receiver, wherein the mean light path between the radiation emitter and radiation receiver corresponds to the effective absorption length;
(d) transilluminating the body fluid in the measuring area;
(e) actively and in a defined manner periodically changing the effective absorption length through the body fluid between the radiation emitter and receiver, without using the body fluid as a medium for transmission of forces;
(f) detecting changes in light intensity of at least two spectral frequencies which are characteristic absorption frequencies for said substance of a body fluid to be detected, said changes constituting a ratio "Ω" of said substance of a body fluid to be detected, wherein Ω is defined with the following equation:

$$\Omega = \frac{\ln\left(\frac{I_{out\,max\,\lambda 1}}{I_{out\,min\,\lambda 1}}\right)}{\ln\left(\frac{I_{out\,max\,\lambda 2}}{I_{out\,min\,\lambda 2}}\right)} ; \text{ and}$$

(g) determining a correlation between (i) said ratio Ω and (ii) a parameter of said substance of a body fluid, wherein at least one of said emitter and receiver is provided with an optically transparent layer for reducing the effective non-pulsatile absorption length of the body fluid.

18. A process for in vitro validation of a photometric device, said method comprising:
(a) specifying a substance of a body fluid to be measured;
(b) adjusting a parameter of said substance of a body fluid in body fluid in vitro;
(c) providing adjusted body fluid from step (b) to a measuring area such that at least some of said adjusted body fluid is between a radiation emitter and a radiation receiver, wherein the mean light path between the radiation emitter and radiation receiver corresponds to the effective absorption length;
(d) transilluminating the body fluid in the measuring area;
(e) actively and in a defined manner periodically changing the effective absorption length through the body fluid between the radiation emitter and receiver, without using the body fluid as a medium for transmission of forces;
(f) detecting changes in light intensity of at least two spectral frequencies which are characteristic absorption frequencies for said substance of a body fluid to be detected, said chances constituting a ratio "Ω" of said substance of a body fluid to be detected, wherein Ω is defined with the following equation:

$$\Omega = \frac{\ln\left(\frac{I_{out\,max\,\lambda 1}}{I_{out\,min\,\lambda 1}}\right)}{\ln\left(\frac{I_{out\,max\,\lambda 2}}{I_{out\,min\,\lambda 2}}\right)} ; \text{and}$$

(g) determining a correlation between (i) said ratio $\Omega$ and (ii) a parameter of said substance of a body fluid, further comprising dispersing color neutral plastic scattering particles in the body fluid to increase the scattering properties of said body fluid for better tissue imitation, wherein said scattering particles have approximately the specific density of the body fluid.

19. A device for in vitro validation of a photometric device by a method comprising:
    (a) specifying a substance of a body fluid to be measured;
    (b) adjusting the concentration parameter of said substance of a body fluid in body fluid in vitro;
    (c) providing adjusted body fluid from step (b) to a measuring area such that at least some of said adjusted body fluid is between a radiation emitter and a radiation receiver, wherein at least one of said radiation emitter and a radiation receiver are immersed in said body fluid and wherein the mean light path between the radiation emitter and radiation receiver corresponds to the effective absorption length;
    (d) transilluminating the body fluid in the measuring area;
    (e) actively and in a defined manner periodically changing the effective absorption length through the body fluid between the radiation emitter and receiver, without using the body fluid as a medium for transmission of forces;
    (f) detecting changes in light intensity of at least two spectral frequencies which are characteristic absorption frequencies for said substance of a body fluid to be detected, said changes constituting a ratio "$\Omega$" of said substance of a body fluid to be detected, wherein $\Omega$ is defined with the following equation:

$$\Omega = \frac{\ln\left(\frac{I_{out\,max\,\lambda 1}}{I_{out\,min\,\lambda 1}}\right)}{\ln\left(\frac{I_{out\,max\,\lambda 2}}{I_{out\,min\,\lambda 2}}\right)} ; \text{and}$$

(g) determining a correlation between (i) said ratio $\Omega$ and (ii) a parameter of said substance of a body fluid;
said device for in vitro validation of a photometric device comprising:
    at least one device for adjusting the parameter of a substance of a body fluid to be measured;
    at least one measuring area;
    a transport device, with which the body fluid with the adjusted concentration is brought into said measuring area;
    at least one radiation emitter and at least one radiation receiver provided in said measuring area;
    means for periodically varying the mean effective light path between the radiation emitter and at least one radiation receiver, without using the body fluid as a medium for transmission of forces on the emitter and/or receiver; and
    a device which converts a read-out of a light intensity as detected by means of said radiation receiver at at least one spectral frequency into the form of at least one parameter, which light has traveled from said radiation emitter to said radiation receiver through the body fluid, and brings about a correlation between (i) the concentration and (ii) the parameter.

20. A device according to claim 19, wherein an optical displacement body with variable thickness is provided in the optical path between the emitter and receiver and is provided with means for moving between a first and a second position for actively and in a defined manner periodically changing the effective absorption length through the body fluid between the radiation emitter and receiver, without using the body fluid as a medium for transmission of forces.

21. A process for in vitro validation of a photometric device, said method comprising:
    (a) specifying a substance of a body fluid to be measured;
    (b) adjusting a parameter of said substance of a body fluid in body fluid in vitro;
    (c) providing adjusted body fluid from step (b) to a measuring area within a measuring cell such that at least some of said adjusted body fluid is between a radiation emitter and a radiation receiver, wherein said radiation emitter and radiation receiver are immersed within said body fluid, and wherein the mean light path between the radiation emitter and radiation receiver corresponds to the effective absorption length;
    (d) transilluminating the body fluid in the measuring area;
    (e) actively and in a defined manner periodically changing the effective absorption length through the body fluid between the radiation emitter and receiver, without using the body fluid as a medium for transmission of forces;
    (f) detecting changes in light intensity of at least two spectral frequencies which are characteristic absorption frequencies for said substance of a body fluid to be detected, said changes constituting a ratio "$\Omega$" of said substance of a body fluid to be detected, wherein $\Omega$ is defined with the following equation:

$$\Omega = \frac{\ln\left(\frac{I_{out\,max\,\lambda 1}}{I_{out\,min\,\lambda 1}}\right)}{\ln\left(\frac{I_{out\,max\,\lambda 2}}{I_{out\,min\,\lambda 2}}\right)} ; \text{and}$$

(g) determining a correlation between (i) said ratio $\Omega$ and (ii) a parameter of said substance of a body fluid.

* * * * *